US006528529B1

(12) United States Patent
Brann et al.

(10) Patent No.: US 6,528,529 B1
(45) Date of Patent: Mar. 4, 2003

(54) COMPOUNDS WITH ACTIVITY ON MUSCARINIC RECEPTORS

(75) Inventors: Mark Brann, San Diego, CA (US); Terri Messier, Burlington, VT (US); Erika Currier, San Diego, CA (US); Kate Duggento, San Diego, CA (US); Tracy Spalding, San Diego, CA (US); Mikael Friberg, Bronshoj (DK); Niels Skjaerbaek, Copenhagen (DK)

(73) Assignee: Acadia Pharmaceuticals Inc., San Diego, CA (US)

( * ) Notice: Subject to any disclaimer, the term of this patent is extended or adjusted under 35 U.S.C. 154(b) by 0 days.

(21) Appl. No.: 09/356,202

(22) Filed: Jul. 16, 1999

Related U.S. Application Data

(63) Continuation-in-part of application No. 09/282,778, filed on Mar. 31, 1999, now abandoned.
(60) Provisional application No. 60/080,133, filed on Mar. 31, 1998.

(51) Int. Cl.[7] .................. A61K 31/445; C07D 211/14
(52) U.S. Cl. ...................... 514/317; 546/237
(58) Field of Search ............................ 546/237; 514/317

(56) References Cited

U.S. PATENT DOCUMENTS

| | | | |
|---|---|---|---|
| 2,126,329 A | 8/1938 | Hoffer | 260/43 |
| 2,400,913 A | 5/1946 | Burger | 260/333 |
| 2,695,295 A | 11/1954 | Swain | 260/268 |
| 3,816,433 A | 6/1974 | Hernestam et al. | 260/293.8 |
| 3,912,743 A | 10/1975 | Christensen et al. | 260/293.58 |
| 4,045,566 A | 8/1977 | Archibald et al. | 424/267 |
| 4,992,457 A | 2/1991 | Schulman et al. | 514/376 |
| 5,093,333 A | 3/1992 | Saab | 514/235.2 |
| 5,175,166 A | 12/1992 | Dunbar et al. | 514/275 |
| 5,177,077 A | 1/1993 | Hohlweg et al. | 514/252 |
| 5,276,035 A | 1/1994 | Hohlweg et al. | 514/252 |
| 5,403,845 A | 4/1995 | Dunbar et al. | 514/275 |
| 5,468,875 A | 11/1995 | Sabb et al. | 548/512 |
| 5,470,850 A | 11/1995 | Foged et al. | 514/213 |
| 5,510,478 A | 4/1996 | Sabb | 540/585 |
| 5,512,562 A | 4/1996 | Hohlweg et al. | 514/215 |
| 5,534,522 A | 7/1996 | Ando et al. | 514/299 |
| 5,571,819 A | 11/1996 | Sabb et al. | 514/303 |
| 5,726,179 A | 3/1998 | Messer, Jr. et al. | 514/256 |
| 5,756,501 A | 5/1998 | Sabb | 514/248 |
| 5,834,458 A | 11/1998 | Mitch | 514/200 |

FOREIGN PATENT DOCUMENTS

| | | |
|---|---|---|
| BE | 610830 | 5/1962 |
| DE | 2259004 | 6/1973 |
| DE | 3706585 A1 | 9/1988 |
| DE | 42 34 198 | 4/1994 |
| EP | 0 332 570 A2 | 9/1989 |
| EP | 384285 | 4/1991 |
| EP | 0 514 277 | 11/1992 |
| EP | 370415 | 6/1993 |
| EP | 647642 | 4/1995 |
| EP | 311313 | 5/1995 |
| EP | 384288 | 5/1995 |
| EP | 709381 | 5/1996 |
| EP | 723781 | 7/1996 |
| EP | 727208 | 8/1996 |
| EP | 727209 | 8/1996 |
| EP | 429344 | 9/1996 |
| EP | 805153 | 11/1997 |
| EP | 0 805 153 | 11/1997 |
| FR | 1382425 | 3/1965 |
| FR | 1543944 | 9/1968 |
| FR | 1570446 | 6/1969 |
| FR | 2261008 | 9/1975 |
| GB | 874206 | 8/1961 |
| GB | 1142143 | 2/1969 |
| JP | 61280497 | 12/1986 |
| JP | 6298732 | 10/1994 |
| JP | 6305967 | 11/1994 |
| NL | 6603799 | 9/1966 |
| WO | WO 93/00313 | 1/1993 |
| WO | WO 93/14089 | 7/1993 |
| WO | WO 93/18772 | 9/1993 |
| WO | WO 94/22861 | 10/1994 |
| WO | WO 09/00131 | 1/1995 |
| WO | WO 95/31457 | 11/1995 |
| WO | WO 96/03377 | 2/1996 |
| WO | WO 96/19479 | 6/1996 |
| WO | WO 96/26196 | 8/1996 |
| WO | WO96/38422 | 12/1996 |
| WO | WO 96/40687 | 12/1996 |
| WO | WO 97/00894 | 1/1997 |
| WO | WO 97/40044 | 10/1997 |
| WO | WO 97/40045 | 10/1997 |
| WO | WO 98/00412 | 1/1998 |
| WO | WO 98/05292 | 2/1998 |
| WO | WO 98/06697 | 2/1998 |
| WO | WO 98/47900 | 10/1998 |
| WO | WO 99/17771 | 4/1999 |
| WO | WO99/50247 | 10/1999 |

OTHER PUBLICATIONS

Rieu et al., Chemical Abstracts, vol. 124:117095, 1995.*
Van Daele, Chemical Abstracts, vol. 99:194812, 1983.*
Carr et al., Chemical Abstracts, vol. 94:156759, 1981.*
Ono, Chemical Abstracts, vol. 88:105329, 1978.*
Sasajima et al., Chemical Abstracts, vol. 85:192375, 1976.*
Glozman et al., Chemical Abstracts, vol. 71:61134, 1969.*
Albrecht et al., Chemical Abstracts, vol. 110:114683, 1989.*
Lafon, Chemical Abstracts, vol. 101:151764, 1984.*

(List continued on next page.)

*Primary Examiner*—Richard L. Raymond
(74) *Attorney, Agent, or Firm*—Knobbe Martens Olson & Bear LLP

(57) ABSTRACT

Compounds and methods are provided for the alleviation or treatment of diseases or conditions in which modification of muscarinic m1 receptor activity has a beneficial effect. In the method, a therapeutically effective amount of a selective muscarinic m1 agonist compound is administered to a patient in need of such treatment.

88 Claims, 2 Drawing Sheets

OTHER PUBLICATIONS

Fleming, Chamical Abstracts, vol. 87:84839, 1977.*

Aktiebolog Ferrosan, Chemical Abstracts, vol. 66:37775v, 1967.*

Hernestam et al., Chemical Abstracts, vol. 96:110159, 1982.*

Jeanjean et al., Society of Biological Psychiatry, vol. 41, pp. 1010–1019 "Neuroleptic Binding to Sigma Receptors: Possible Involvement in Neuroleptic–Induced Acute Dystonia" (1997).

Bolden et al., The J. of Pharmacology and Experimental Therapeutics "Antagonism by Antimuscarinic and Neuroleptic Compounds at the Five Cloned Human Muscarinic Cholinergic Receptors Expressed in Chinese Hamster Ovary Cells" vol. 260, No. 2, pp. 576–580 (1992).

Chemical Abstracts, vol. 123, No. 23, Dec. 4, 1995 (Dec. 4, 1995) Columbus, Ohio, US; abstract No. 313689, Gail Rene: "Labeling of muscarinic antagonists of the tertiary fluorophenylcarbinol and –silano types with the positron emitters carbon–11 and fluorine–18" XP002156290 abstract 169807–59–4 & Ber. Forschungszent. Juelich (1995), Jeul–3029, 147 PP.

McElvain et al., "Piperidine Derivatives. XVII. Local Anesthetics Derived from Substituted Piperidinoalcohols" vol. 68, pp. 2592–2600 (1946).

Bailey et al., "Piperidine Derivatives. VIII. Substituted Piperidino–Alkyl Benzoates" pp. 1633–1640 (1930).

International Search Report for PCT/US00/19366 Mailed on Mar. 14, 2001.

Aldous, F.A.B., Structure–Activity Relationships in Psychotomimetic Phenylalkylamines. J. Med. Chem. 17:1100–1111 (1974).

Bonner et al., Identification of a Family of Muscarinic Acetylcholine Receptor Genes. Science 237:527–532 (1987).

Bonner et al., Cloning and Expression of the Human and Rat m5 Muscarinic Acetylcholine Receptor Genes. Neuron 1:403–410 (1988).

Bossier et al., Substituted benzylamines. Chem. Abstr. 66:46195h (1967).

Bossier et al., New derivatives of phenylisopropylamine: synthesis and anorexigenic activity. Chem. Abstr. 67:21527a (1967).

Burckhalter et al., Antiamebic Agents. V.[1] Promising Basic Amebicides Derived from 5–Chloro–8–quinolinol. J. Org. Chem. 26:4070–4076 (1961).

Conde et al., Effects of Thiophene Analogues of Chloramphetamines on Central Serotonergic Mechanisms. J. Med. Chem. 21:978–981 (1978).

Fuller et al., Inhibition of Phenethanolamines N–Methyl Transferase by Ring–Substituted $_\alpha$–Methylphenethylamines (Amphetamines). J. Med. Chem. 14:322–325 (1971).

Fuller et al., Effect of some lipid–soluble derivatives of amphetamine on amphetamine levels in rat brain. J. Pharm. Pharmacol. 25:828–829 (1973).

Fuller et al., Comparison of 4–Chloro–, 4–Bromo– and 4–Fluoroamphetamine in Rats: Drug Levels in Brain and Effects on Brain Serotonin Metabolism. Neuropharmacology 14:739–746 (1975).

Foye et al., Heterocyclic analogs of Amphetamine: Thioureas, Dithiocarbamates, and Negatively Substituted Amides. J. Pharm. Sci. 68:591–595 (1979).

Iversen, Behavioural Evaluation of Cholinergic Drugs. Life Sciences 60(13/14):1145–1152 (1997).

Lukovits et al., Comparative Studies on Drug–Receptor Binding of Phenylethylamine Derivatives Using Calculated Group Contribution Constants. Int. J. Quantum Chem. 20:429–438 (1981).

Law, B., Analysis of Basic Compounds on a Silica Column with an Aqueous Methanol Eluent; The Use o Quantitative Structure–Retention Relationships in Metabolite Identification. J. Cromatog. 407:1–18 (1987).

Avery et al., Potential Role of Muscarinic Agonists in Alzheimer's Disease. Drugs & Aging 11(6):450–459 (1997).

Brauner–Osborne et al., Annulated Heterocyclic Bioisosters of Norarecoline Synthesis and Molecular Pharmacology at Five Recombinant Human Muscarinic Acetylcholine Receptors. J. Med. Chem. 38:2188–2195 (1995).

Britton et al., The Use of 2–Pipecoline in the Mannich Reaction. J. Am. Pharm. Ass'n 43:641–643 (1954).

Brown et al., Muscarinic Receptor Agonists and Antagonists. Goodman & Gilman's The Pharmacological Basis of Therapeutics 141–160 (McGraw–Hill 1996).

Burger et al., Tetrahydrofuryl Amino Alcohols. J. Am. Chem. Soc. 65(12):2382–2383 (1943).

Burger et al., Iodinated Dialkylaminoalkyl Pyridyl Ethers. J. Am. Chem. Soc. 68(3):520 (1946).

Honkanen et al., Synthesis and Antihypertensive Activity of Some New Quinazoline Derivatives. J. Med. Chem. 26:1433–1438 (1983).

Jaen et al., In Vitro and In Vivo Evaluation of the Subtype–Selective Muscarinic Agonist PD 1518332. Life Sciences 56(11/12):845–852 (1995).

Jones et al., Muscarinic Acetylcholine Receptors. Molecular Biology of G–Protein–Coupled Receptors 170–189 (Birkhauser Boston 1992).

Kaiser et al., Synthesis and Antimuscarinic Activity of Some 1–Cycloalkyl–1–hydroxy–1–phenyl–3–(4–substituted piperazinyl)–2–propanones and Related Compounds. J. Med. Chem. 36:610–616 (1993).

Kasa et al., The Cholinergic System in Alzheimer's Disease. Progress in Neurobiology 52:511–535 (1997).

Levey, Allan I. Muscarinic Acetylcholine Receptor Expression in Memory Circuits: Implications for Treatment of Alzheimer Disease. Proc. Natl. Acad. Sci. USA 93:13541–13546 (1996).

Paris et al., N–aminomethylation en serie thiazolique: application a quelques amino–2 benzothiazoles. Bulletin de la Societe Chimique de France 2:672–673 (1973).

Penni, Elizabeth, Building a Better Aspirin. Science 280:1191–1192 (1988).

Profft, Elmar, Zur Kenntnis der $_\beta$–(4–Athylpiperidino)–4–alkoxypropiophenonhydrochloride. Arzneimittel Forschung. Drug Research 8(5): 268–270 (1958).

Standaert et al., Treatment of Central Nervous System Degenerative Disorders. Goodman & Gilman's The Pharmacological Basis of Therapeutics 503–519 (McGraw–Hill 1996).

Sunderland et al., Differential Responsivity of Mood, Behavior, and Cognition to Cholinergic Agents in Elderly Neuropsychiatric Populations. Brain Research Reviews 13:371–389 (1988).

Taylor, Palmer, Anticholinesterase Agents. Goodman & Gilman's The Pharmacological Basis of Therapeutics 161–176 (McGraw–Hill 1996).

Truitt et al., Antitubercular Studies. IV. Derivatives of 1–(4–Nitrophenacyl)–4–alkypyridium Bromides. J. Am. Chem. Soc. 74(21):5448–5449 (1952).

Walker et al., Application of Sodium Borohydride Reduction to Synthesis of Substituted Aminopiperidines, Aminopiperazines, Aminopyridines, and Hydrazines J. Org. Chem. 26(8):2740–2747 (1961).

* cited by examiner

COMPOUNDS WITH ACTIVITY ON MUSCARINIC RECEPTORS

This application claims benefit of copending U.S. Provisional Application Ser. No. 60/080,133 filed Mar. 31, 1998, and is a continuation-in-part of U.S. Ser. No. 09/282,778, which was filed Mar. 31, 1999, now abandoned.

FIELD OF THE INVENTION

The subject matter of this application is also related to the following commonly assigned and copending application by the inventors hereof: International Application No. PCT/US99/07057.

The present invention relates to novel compounds which are selective for muscarinic acetylcholine receptor subtypes, as well as to methods for activating muscarinic receptors and for treating or alleviating diseases in which modification of muscarinic receptor activity is beneficial.

BACKGROUND OF THE INVENTION

Muscarinic acetylcholine receptors play a central role in the central nervous system for higher cognitive functions, as well as in the peripheral parasympathetic nervous system. Cloning has established the presence of five distinct muscarinic receptor subtypes (termed m1–m5) (cf. T. I. Bonner et al, *Science* 237, 1987, pp. 527–532; T. I. Bonner et al., *Neuron* 1, 1988, pp. 403–410). It has been found that m1 is the predominant subtype in the cerebral cortex and is believed to be involved in the control of cognitive functions, m2 is predominant in heart and is believed to be involved in the control of heart rate, m3 is believed to be involved in gastrointestinal and urinary tract stimulation as well as sweating and salivation, m4 is present in brain, and m5 is present in brain and may be involved certain functions of the central nervous system associated with the dopaminergic system.

Animal studies of various muscarinic ligands (S. Iversen, *Life Sciences* 60 (Nos. 13/14), 1997, pp. 1145–1152) have shown that muscarinic compounds have a profound effect on cognitive functions, e.g. learning and memory. This would suggest a potential utility of muscarinic agonists in the improvement of cognitive functions in diseases characterized by cognitive impairment, both age-related (such as Alzheimer's disease or other dementias) and not age-related (such as attention deficit hyperactivity disorder).

Based on the presence of muscarinic receptor subtypes in various tissues, it would appear that the m1 receptor subtype is the more abundant one in the cerebral cortex, basal ganglia and hippocampus where it accounts for 35–60% of all muscarinic receptor binding sites (cf. A. Levey, *Proc. Natl. Acad. Sci. USA* 93, 1996, pp. 13541–13546). It has been proposed that the m1 (and possibly m4) subtype plays a major role as a postsynaptic muscarinic receptor (located on cholinoceptive neurons in the neocortex and hippocampus) in various cognitive and motor functions and is likely to be a major contributor to the m1 responses measured in these regions of the brain.

It has previously been found that conditions associated with cognitive impairment, such as Alzheimer's disease, are accompanied by selective loss of acetylcholine in the brain. This is believed to be the result of degeneration of cholinergic neurons in the basal forebrain which innervate areas of the association cortex and hippocampus involved in higher processes (cf. S. Iversen, supra). This finding would suggest that such conditions may be treated or at least ameliorated with drugs that augment the cholinergic function in the affected areas of the brain.

Treatment with acetylcholine esterase (AChE) inhibitors such as 9-amino-1,2,3,4-tetrahydroacridine (tacrine) results in an increase of acetylcholine in the brain which indirectly causes stimulation of muscarinic receptors. Tacrine treatment has resulted in a moderate and temporary cognitive improvement in Alzheimer's patients (cf. Kasa et al., supra). On the other hand, tacrine has been found to have cholinergic side effects due to the peripheral acetylcholine stimulation. These include abdominal cramps, nausea, vomiting, diarrhea, anorexia, weight loss, myopathy and depression. Gastrointestinal side effects have been observed in about a third of the patients treated. Tacrine has also been found to cause significant hepatotoxicity, elevated liver transaminases having been observed in about 30% of the patients (cf. P. Taylor, "Anticholinergic Agents", Chapter 8 in *Goodman and Gilman: The Pharmacological Basis of Therapeutics*, $9^{th}$ Ed., 1996, pp. 161–176). The adverse effects of tacrine have severely limited its clinical utility. Another AChE inhibitor, (R,S)-1-benzyl-4-[5,6-dimethoxy-1-indanon-2yl] methylpiperidine.HCl (donepezil), has recently been approved for the treatment of symptoms of mild to moderate Alzheimer's disease (cf. P. Kasa et al, supra). No hepatic damage has been observed for this compound but it has gastrointestinal effects similar to those of tacrine, probably due to stimulation of the m3 receptor caused by elevated parasympathetic tone.

It has previously been suggested that, since the muscarinic m1 receptors in the prefrontal cortex and hippocampus appear to be intact, it may be possible to remedy or at least ameliorate the loss of acetylcholine in Alzheimer's disease patients by administration of drugs acting as agonists on those muscarinic receptors (cf. J. H. Brown and P. Taylor, "Muscarinic Receptor Agonists and Antagonists", Chapter 7 in *Goodman and Gilman: The Pharmacological Basis of Therapeutics*, $9^{th}$ Ed., 1996, p. 147).

The muscarinic agonists (believed to be m1 selective) hitherto suggested for the treatment of Alzheimer's disease, such as arecoline, have not shown greater efficacy in clinical trials than AChE inhibitors (cf. S. V. P. Jones et al., supra). In one study (cf. T. Sunderland et al., *Brain Res. Rev.* 13, 1988, pp. 371–389), arecoline was found to have not so much cognitive enhancing effects as effects on behavioral changes often observed in Alzheimer's disease patients, such as a significant increase in motor activity, significant uplifting of mood, and significant decrease in anergia. However, presumed m1 agonists have later been found to be weak partial agonists selective for the m2 and/or m3 receptor subtypes (H. Bräuner-Osborne et al., *J. Med. Chem.* 38, 1995, pp. 2188–2195). As indicated above, m2 subtype selectivity is presumed to be responsible for the cardiovascular effects observed for these agonists, e.g. tachycardia and bradycardia, and m3 activity is believed to account for the adverse gastrointestinal effects of the agonists.

m2 and/or m3 activity is therefore a significant drawback for the muscarinic agonists proposed until now for the treatment of Alzheimer's disease, severely limiting the doses of the drugs which it has been possible to administer to patients who may therefore have received sub-optimal doses. Furthermore, the lack of subtype selectivity and low potency of the currently tested cholinergic compounds appear to favor the negative peripheral side effects and have limited cognitive effects because of weak and/or opposing actions in the brain. It would therefore be of great advantage to develop compounds which have an improved selectivity for the m1 subtype, but which have little or no activity on the m2 and m3 subtypes.

SUMMARY OF THE INVENTION

The present invention provides compounds with muscarinic agonist activity of the general formula (I):

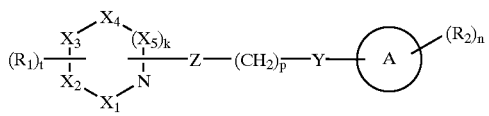

wherein
$X_1$, $X_2$, $X_3$, $X_4$ and $X_5$ are selected from C, N and O;
k is 0 or 1;
t is 0, 1 or 2;
$R_1$ is straight or branched-chain $C_{1-8}$ alkyl, $C_{2-8}$ alkenyl, $C_{2-8}$ alkynyl, $C_{1-8}$ alkylidene, $C_{1-8}$ alkoxy, $C_{1-8}$ heteroalkyl, $C_{1-8}$ aminoalkyl, $C_{1-8}$ haloalkyl, $C_{1-8}$ alkoxycarbonyl, $C_{1-8}$ hydroxyalkoxy, $C_{1-8}$ hydroxyalkyl, —SH, $C_{1-8}$ alkylthio, —O—$CH_2$—$C_{5-6}$ aryl, —C(O)—$C_{5-6}$ aryl substituted with $C_{1-3}$ alkyl or halo; $C_{5-6}$ aryl or $C_{5-6}$ cycloalkyl optionally comprising 1 or more heteroatoms selected from N, S and O; —C(O)$NR_3R_4$, —$NR_3R_4$, —$NR_3C(O)NR_4R_5$, —$CR_3R_4$, —OC(O)$R_3$, —(O)(CH$_2$)$_s$$NR_3R_4$ or —(CH$_2$)$_s$$NR_3R_4$; where $R_3$, $R_4$ and $R_5$ are the same or different, each independently being selected from H, $C_{1-6}$ alkyl; $C_{5-6}$ aryl optionally comprising 1 or more heteroatoms selected from N, O and S, and optionally substituted with halo or $C_{1-6}$ alkyl; $C_{3-6}$ cycloalkyl; or $R_3$ and $R_4$ together with the N atom, when present, form a cyclic ring structure comprising 5–6 atoms selected from C, N, S and O; and s is an integer from 0 to 8;

A is $C_{5-12}$ aryl or $C_{5-7}$ cycloalkyl, each optionally comprising 1 or more heteroatoms selected from N, S and O;

$R_2$ is H, amino, hydroxyl, halo, or straight or branched-chain $C_{1-6}$ alkyl, $C_{2-6}$ alkenyl, $C_{2-6}$ alkynyl, $C_{1-6}$ alkoxy, $C_{1-6}$ heteroalkyl, $C_{1-6}$ aminoalkyl, $C_{1-6}$ haloalkyl, $C_{1-6}$ alkylthio, $C_{1-6}$ alkoxycarbonyl, —CN, —CF$_3$, —OR$_3$, —COR$_3$, NO$_2$, —NHR$_3$, —NHC(O)$R_3$, —C(O)$NR_3R_4$, —$NR_3R_4$, —$NR_3C(O)NR_4R_5$, —OC(O)$R_3$, —C(O)$R_3R_4$, —O(CH$_2$)$_q$NR$_3$, —CNR$_3R_4$ or —(CH$_2$)$_q$$NR_3R_4$; where q is an integer from 1 to 6;

n is 0, 1, 2, 3 or 4, the groups $R_2$, when n>1, being the same or different;

p is 0 or an integer from 1 to 5;

Y is O, S, CHOH, —NH(CO)—, —C(O)NH—, —C(O)—, —OC(O)—, NR$_7$ or —CH=N—, and $R_7$ is H or $C_{1-4}$ alkyl; or absent; and Z is $CR_8R_9$ wherein $R_8$ and $R_9$ are independently selected from H, and straight or branched chain $C_{1-8}$ alkyl; or a pharmaceutically acceptable salt, ester or prodrug thereof.

The present invention further provides pharmaceutical compositions comprising an effective amount of a compound of formula (I).

Further provided are methods of treating the symptoms of a disease or condition associated with reduced levels of acetylcholine, said method comprising administering a therapeutically effective amount of a composition comprising a compound of formula (I).

In yet a further embodiment, the present invention provides a method of treating the symptoms of a disease or condition associated with increased intraocular pressure, such as, for example, glaucoma, where the method comprises administering a therapeutically effective amount of a composition comprising a muscarinic receptor agonist, preferably an m1 selective agonist, preferably selected from the compounds of formula (I).

DETAILED DESCRIPTION OF THE INVENTION

Figure 1:
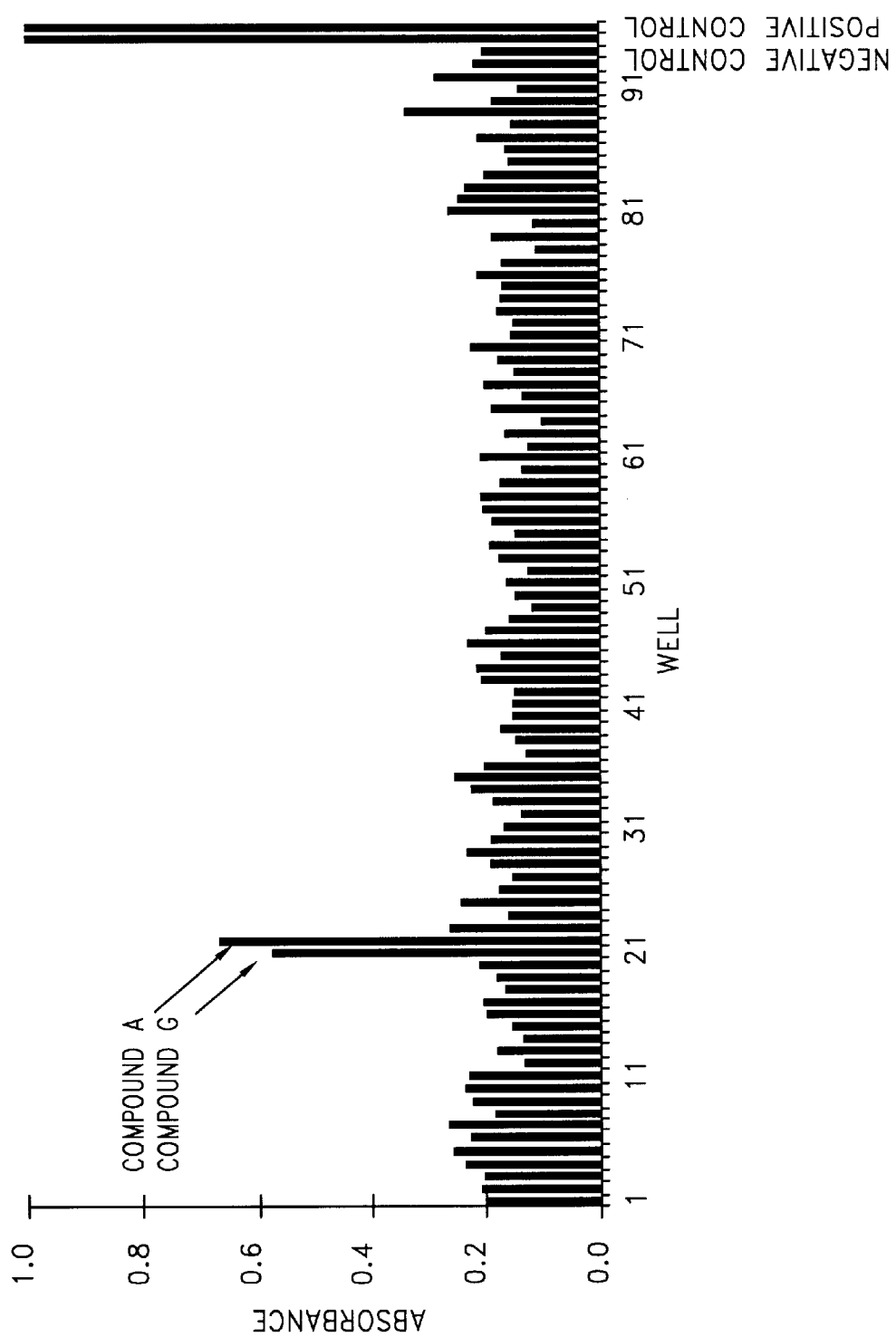
FIG. 1 is a graph showing raw data from one 96-well microtiter plate of screening of 35,000 small organic molecules in the assay described in Example XVI.

The present invention provides compounds preferably showing a relatively high selectivity towards the m1 receptor subtype relative to other muscarinic subtypes which may have a beneficial effect in the treatment of cognitive impairment such as Alzheimer's disease or other conditions associated with age-related cognitive decline while avoiding the adverse affects of the drugs hitherto suggested for this purpose. Compounds exhibiting this property have surprisingly been isolated by screening against m1–m5 receptor subtypes.

According to one embodiment, the present invention provides compounds of formula (I), wherein $X_1$, $X_2$, $X_3$, $X_4$ and $X_5$ are C; or one of $X_1$, $X_2$, $X_3$, $X_4$ or $X_5$ is O or N and the other are C;

k is 0 or 1;

t is 1;

$R_1$ is straight or branched-chain $C_{1-8}$ alkyl, $C_{2-8}$ alkenyl, $C_{2-8}$ alkynyl, $C_{1-8}$ alkylidene, $C_{1-8}$ alkoxy, $C_{1-8}$ aminoalkyl, $C_{1-8}$ haloalkyl, $C_{1-8}$ alkoxycarbonyl, —C(O)$NR_3R_4$, —$NR_3R_4$, —$NR_3C(O)NR_4R_5$, —OC(O)$R_3$, or —(CH$_2$)$_s$$NR_3R_4$; where $R_3$, $R_4$ and $R_5$ are the same or different, each independently being selected from H and $C_{1-6}$ alkyl; and s is an integer from 1 to 8;

n is 1, 2 or 3; and

A is phenyl or naphthyl;

where $R_2$ is straight or branched-chain $C_{1-6}$ alkyl, $C_{2-6}$ alkenyl, $C_{2-6}$ alkynyl, $C_{1-6}$ alkoxy, $C_{1-6}$ aminoalkyl, $C_{1-6}$ haloalkyl, $C_{1-6}$ alkoxycarbonyl, —CN, —CF$_3$, —OH, —COR$_3$, —NHR$_3$, —NHC(O)$R_3$, —C(O)$NR_3R_4$, —$NR_3R_4$, —$NR_3C(O)NR_4R_5$, —OC(O)$R_3$, or —(CH$_2$)$_q$$NR_3R_4$; where q is an integer from 1 to 6; or A is aryl comprising 1 or more heteroatoms selected from N, S and O;

$R_2$ is H, halo, straight or branched-chain $C_{1-6}$ alkyl, $C_{2-6}$ alkenyl, $C_{2-6}$ alkynyl, $C_{1-6}$ alkoxy, $C_{1-6}$ heteroalkyl, $C_{1-6}$ aminoalkyl, $C_{1-6}$ haloalkyl, $C_{1-6}$ alkoxycarbonyl, —CN, —CF$_3$, OH, —COR$_3$, —NHR$_3$, —NHC(O)$R_3$, —C(O)$NR_3R_4$, —$NR_3R_4$, —$NR_3C(O)NR_4R_5$, —OC(O)$R_3$ or —(CH$_2$)$_q$$NR_3R_4$; or a pharmaceutically acceptable salt, ester or prodrug thereof.

In one preferred embodiment, the compound is of the formula (II):

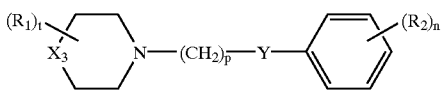

Preferred subgeneric embodiments of compounds of formula (II) include compounds of formulas (IIa) and (IIb):

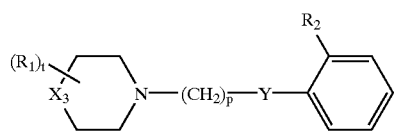

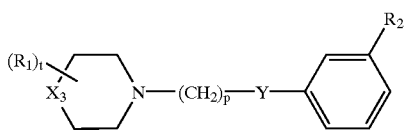

According to one preferred series of embodiments of compounds of formulas I, II, IIa and IIb, t is 1 and Y is —C(O)—, —NHC(O)—, S, O or —OC(O)—. In another, $X_3$ is C. Preferably, $R_1$ is alkyl, where preferably $R_2$ is alkyl, aminoalkyl, alkoxy or hydroxyl. In one embodiment, p is 3. In another, $R_1$ is $C_{2-8}$ alkyl and $R_2$ is methyl, hydroxyl or alkoxy.

In one embodiment, n is 1 or 2; Y is —C(O)— or O and t is 1. Preferably, $R_2$ is halo. According to other embodiments, t is 0; or $R_1$ is alkoxy, benzyl or phenyl.

$X_3$ may also be N, where according to one embodiment, $R_1$ is alkyl or alkoxy; or $R_1$ is benzyl or phenyl; where $R_2$ is alkyl or alkoxy.

According to another embodiment, $X_3$ is O, where t may be, for example, 0. Preferably, $R_2$ is alkyl or alkoxy; or $R_2$ is halo.

Particular embodiments of the invention include:
4-Methoxy-1-[4-(2-methylphenyl)-4-oxo-1-butyl]piperidine;
4-Ethoxy-1-[4-(2-methylphenyl)-4-oxo-1-butyl]piperidine;
4-Propoxy-1-[4-(2-methylphenyl)-4-oxo-1-butyl]piperidine;
4-Butoxy-1-[4-(2-methylphenyl)-4-oxo-1-butyl]piperidine;
4-Methoxymethyl-1-[4-(2-methylphenyl)-4-oxo-1-butyl]piperidine;
4-Ethoxymethyl-1-[4-(2-methylphenyl)-4-oxo-1-butyl]piperidine;
4-Propoxymethyl-1-[4-(2-methylphenyl)-4-oxo-1-butyl]piperidine;
4-(2-Methoxyethyl)-1-[4-(2-methylphenyl)-4-oxo-1-butyl]piperidine;
4-(2-Ethoxyethyl)-1-[4-(2-methylphenyl)-4-oxo-1-butyl]piperidine;
4-Methoxy-4-methyl-1-[4-(2-methylphenyl)-4-oxo-1-butyl]piperidine;
4-Methoxy-4-ethyl-1-[4-(2-methylphenyl)-4-oxo-1-butyl]piperidine;
4-Methoxy-4-propyl-1-[4-(2-methylphenyl)-4-oxo-1-butyl]piperidine;
4-Methoxy-4-n-butyl-1-[4-(2-methylphenyl)-4-oxo-1-butyl]piperidine;
4-Ethoxy-4-methyl-1-[4-(2-methylphenyl)-4-oxo-1-butyl]piperidine;
4-Ethoxy-4-ethyl-1-[4-(2-methylphenyl)-4-oxo-1-butyl]piperidine;
4-Ethoxy-4-propyl-1-[4-(2-methylphenyl)-4-oxo-1-butyl]piperidine;
4-Ethoxy-4-n-butyl-1- [4-(2-methylphenyl)-4-oxo-1-butyl]piperidine;
4-Propoxy-4-methyl-1- [4-(2-methylphenyl)-4-oxo-1-butyl]piperidine;
4-Propoxy-4-ethyl-1-[4-(2-methylphenyl)-4-oxo-1-butyl]piperidine;
4-Propoxy-4-propyl-1-[4-(2-methylphenyl)-4-oxo-1-butyl]piperidine;
4-Propoxy-4-n-butyl-1-[4-(2-methylphenyl)-4-oxo-1-butyl]piperidine;
4-n-Butoxy-4-methyl-1-[4-(2-methylphenyl)-4-oxo-1-butyl]piperidine;
4-n-Butoxy-4-ethyl-1-[4-(2-methylphenyl)-4-oxo-1-butyl]piperidine;
4-n-Butoxy-4-propyl-1-[4-(2-methylphenyl)-4-oxo-1-butyl]piperidine;
4-n-Butoxy-4-n-butyl-1-[4-(2-methylphenyl)-4-oxo-1-butyl]piperidine;
2-[3-(4-n-Butylpiperidine)propoxy]toluene;
2-[3-(4-n-Butylpiperidine)propanesulfanyl]toluene;
2-[3-(4-n-Butylpiperidine)propanesulfinyl]toluene;
3-(4-n-Butylpiperidine)-o-tolyl-butane-1-thione;
3-(4-n-Butylpiperidinopropyl)-o-tolyl-amine;
N-(4-(4-n-Butylpiperidine)-1-o-tolyl-butyl)-hydroxylamine;
4n-Butyl-1-[4-(2-chlorophenyl)-4-oxo-1-butyl]piperidine;
4-n-Butyl-1-[4-(2-bromophenyl)-4-oxo-1-butyl]piperidine;
4-n-Butyl-1-[4-(2-fluorophenyl)-4-oxo-1-butyl]piperidine;
4-n-Butyl-1-[4-(2-mercaptophenyl)-4-oxo-1-butyl]piperidine;
4-n-Butyl-1-[4-(2-sulfanylmethylphenyl)-4-oxo-1-butyl]piperidine;
4-n-Butyl-1-[4-(2-sulfanylethylphenyl)-4-oxo-1-butyl]piperidine;
4-n-Butyl-1-[4-(2-aminophenyl)4-oxo-1-butyl]piperidine;
4-n-Butyl-1-[4-(2-methylaminophenyl)-4-oxo-1-butyl]piperidine;
4-n-Butyl-1-[4-(2-ethylaminophenyl)-4-oxo-1-butyl]piperidine;
4-n-Butyl-1-[4-(2-dimethylaminophenyl)-4-oxo-1-butyl]piperidine;
4-n-Butyl-1-[4-(2-diethylaminophenyl)-4-oxo-1-butyl]piperidine;
4-n-Butyl-1-[4-(1-H-imidazol-2-yl)-4-oxo-1-butyl]piperidine;
4-n-Butyl-1-[4-(1-imidazol-1-yl)-4-oxo-1-butyl]piperidine;
4-n-Butyl-1-[4-(1-thiazol-2-yl)-4-oxo-1-butyl]piperidine;
4-n-Butyl-1-[4-([1,2,3]triazol-1-yl)-4-oxo-1-butyl]piperidine;
2-[4-n-butyl-piperidine-1-ethyl]-8-methyl-3,4-dihydro-2H-naphthalen-1-one;
2-[4-n-butyl-piperidine-1-ethyl]-7-methyl-indan-1-one;
3-[4-n-butyl-piperidine-1-ethyl]-chroman-4-one;
2-[4-n-butyl-piperidine-1-ethyl]-1H-benzoimidazole;
4-n-Butyl-1-[4-(4-fluoro-2-methylphenyl)-4-oxo-1-butyl]piperidine;
4-n-Butyl-1-[4-(2-hydroxyphenyl)-4-oxo-1-butyl]piperidine;
4-n-Butyl-1-[4-(2-methoxylphenyl)-4-oxo-1-butyl]piperidine;
4-n-Butyl-1-[4-(1-thiophen-2-yl)-4-oxo-1-butyl]piperidine;
4-n-Butyl-1-[4-(2-ethylphenyl)-4-oxo-1-butyl]piperidine;
4-n-Butyl-1-[4-(2-ethoxyphenyl)-4-oxo-1-butyl]piperidine;
4-n-Butyl-1-[4-(2,4-direthylphenyl)-4-oxo-1-butyl]piperidine;
4-n-Butyl-1-[4-(2,3-direthylphenyl)-4-oxo-1-butyl]piperidine;

4-n-Butyl-1-[4-(3-dmethoxyphenyl)-4-oxo-1-butyl] piperidine;
4-n-Butyl-1-[4-(2-benzyloxyphenyl)-4-oxo-1-butyl] piperidine;
4-n-Butyl-1- [4-(4-methylphenyl)-4-oxo-1-butyl]piperidine;
4-n-Butyl-N-phenyl-butyramide;
4-Methyl-1- [4-(2-methylphenyl)-4-oxo-1-butyl]piperidine;
4-n-Butyl-1-[4-(naphthalen-1-yl)-4-oxo-1-butyl]piperidine;
4-Benzyl-1-[4-(2-methylphenyl)-4-oxo-1-butyl]piperidine;
1-[4-(2-methylphenyl)-4-oxo-1-butyl]pyrrolidine;
4-Benzyl-1-[4-(2-methylphenyl)-4-oxo-1-butyl]piperazine;
2-Propyl-1-[4-(2-methylphenyl)-4-oxo -1-butyl]piperidine ;
2-Ethyl-1-[4-(2-methylphenyl)-4-oxo-1-butyl]piperidine;
4-n-Propyl-1-[4-(2-methylphenyl)-4-oxo-1-butyl] piperazine;
3,5-Dimethyl-1-[4-(2-methylphenyl)-4-oxo-1-butyl] piperidine;
4-Methyl-1-[4-(2-methylphenyl)-4-oxo-1-butyl]piperazine;
4-n-Hexyl-1- [4-(2-methylphenyl)-4-oxo-1-butyl] piperazine;
4-Hydroxyethyl-1-[4-(2-methylphenyl)-4-oxo-1-butyl] piperazine;
4-Ethyl-1-[4-(2-methylphenyl)-4-oxo-1-butyl]piperazine;
4-Benzyl-1-[4-(4-fluorophenyl)-4-oxo-1-butyl]piperidine;
4-Benzyl-1-[4-(4-bromophenyl)-4-oxo-1-butyl]piperidine;
4-Phenyl-1-[4-(2-methylphenyl)-4-oxo-1-butyl]piperazine;
3-Hydroxymethyl-1-[4-(2-methylphenyl)-4-oxo-1-butyl] piperidine;
4-Methyl-1-[4-(4-bromophenyl)-4-oxo-1-butyl]piperidine;
1-[4-(2-methylphenyl)-4-oxo-1-butyl]piperidine;
2-Hydroxymethyl-1-[4-(2-methylphenyl)-4-oxo-1-butyl] piperidine;
4-Benzyl-1-[4-(2-methylphenyl)-4-oxo-1-pentyl] piperazine;
4-n-Hexyl-1-[4-(2-methylphenyl)-4-oxo-1-pentyl] piperazine;
4-(Piperidine-1-yl)-1-[4-(2-methylphenyl)-4-oxo-1-butyl] piperidine;
1-[4-(2-methylphenyl)-4-oxo-1-butyl]-2,3-dihydro-1H-indole;
4-Benzyl-1-[5-(2-methylphenyl)-5-oxo-1-pentyl]piperidine;
4-n-Butyl-1-[5-(2-methylphenyl)-5-oxo-1-pentyl] piperidine;
4-n-Butyl-1-[4-(2,6-dimethylphenyl)-4-oxo-1-butyl] piperidine;
4-n-Butyl-1-[4-(2-methoxymethylphenyl)-4-oxo-1-butyl] piperidine;
1-(2-Methylphenyl)-2-(4-benzylpiperazin-1-yl)-ethanone;
3,5-Dimethyl-1-[5-(2-methylphenyl)-5-oxo-1-pentyl] piperidine;
3,5-Dimethyl-1-[4-(4-fluorophenyl)-4-oxo-1-butyl] piperidine;
1-[4-(4-Fluorophenyl)-4-oxo-1-butyl]pyrrolidine;
4-Benzyl-1-[6-(2-methylphenyl)-6-oxo-1-hexyl]piperazine;
3,5-Dimethyl-1-[6-(2-methylphenyl)-6-oxo-1-butyl] piperidine;
4-Benzyl-1-[5-(2-methoxyphenyl)-5-oxo-1-pentyl] piperazine;
4-Benzyl-1-[3-phenyl-3-oxo-1-propyl]piperazine;
4-n-Butyl-1-[5-(2-methoxyphenyl)-5-oxo-1-pentyl] piperidine;
3,5-Dimethyl-1-[4-(4-fluoro-2-methylphenyl)-4-oxo-1-butyl]piperidine;
3-n-Butyl-1-[4-(2-methylphenyl)-4-oxo-1-butyl]piperidine;
4-n-Butyl-1-[4-(2-methylphenyl)-4-oxo-2-methyl-1-butyl] piperidine;
4-n-Butyl-1-[4-(2-methylphenyl)-4-oxo-2,2-dimethyl-1-butyl]piperidine;
4-n-Butyl-1-[4-(2-methylphenyl)-4-oxo-2-ethyl-1-butyl] piperidine;
4-n-Butyl-1-[4-(2-methylphenyl)-4-oxo-2-propyl-1-butyl] piperidine; and
4-n-Butyl-1-[4-(2-methylphenyl)-4-oxo-2,2-diethyl-1-butyl]piperidine.

Compounds per se specifically excluded from the scope of formula I are 4-n-Butyl-1-[4-phenyl-4-oxo-1-butyl] piperidine; 4-n-Butyl-1-[4-(2-methylphenyl)-4-oxo-1-butyl] piperazine; 2-[3-(3-n-Butylpiperidine)propanesulfanyl] toluene; and 4-Propyloxy-1-[4-(4-fluorophenyl)-4-oxo-1-butyl]piperidine (i.e., compounds where —$(CH_2)_p$—Y— is —$(CH_2)_3$—C(O)— or —$(CH_2)_3$—S—; and $X_1$ through $X_5$ are C; such that —A—$(R_2)_n$ and $R_1$ are not together: o-methyl-phenyl and n-butyl, respectively; phenyl and n-butyl, respectively; or p-fluorophenyl and —O—$(CH_2)_2$ $CH_3$, respectively).

The present invention further provides a method of agonizing a muscarinic receptor comprising contacting the receptor with an effective amount of a compound of formula (I), inclusive of all compounds within the scope of formula (I)(i.e., including 4-n-Butyl-1-[4-phenyl-4-oxo-1-butyl] piperidine; 4-n-Butyl-1-[4-(2-methylphenyl)-4-oxo-1-butyl] piperazine; 2-[3-(3-n-Butylpiperidine)propanesulfanyl] toluene; and 4-Propyloxy-1-[4-(4-fluorophenyl)-4-oxo-1-butyl]piperidine).

The present further provides pharmaceutical compositions comprising an effective amount of a compound of formula (I), inclusive of all compounds within the scope of formula (I)(i.e., including -n-Butyl-1-[4-phenyl-4-oxo-1-butyl]piperidine; 4-n-Butyl-1-[4-(2-methylphenyl)-4-oxo-1-butyl]piperazine; 2-[3-(3-n-Butylpiperidine)propanesulfanyl]toluene; and 4-Propyloxy-1-[4-(4-fluorophenyl)-4-oxo-1-butyl]piperidine).

The present invention further also provides methods of treating the symptoms of a disease or condition associated with reduced levels of acetylcholine, the method comprising administering a therapeutically effective amount of a composition described herein. Exemplary diseases or conditions include neurogenerative disease, cognitive impairment, age-related cognitive decline or dementia.

The present invention further provides a method of treating the symptoms of a disease or condition associated with increased intraocular pressure, the method comprising administering a therapeutically effective amount of a muscarinic receptor agonist. Glaucoma is a disease in which an abnormality is observed in the circulation-control mechanism of the aqueous humor filling up the anterior chamber, i.e., the space formed between the cornea and the lens. This leads to an increase in the volume of the aqueous humor and an increase in intraocular pressure, consequently leading to the visual field defect and even to loss of eyesight due to the compulsion and contraction of the papillae of the optic nerve. It has been found that muscarinic receptor agonists, and in particular m1 receptor selective agonists, are effective in reducing intraocular pressure. Thus, in a preferred embodiment, the method comprises administering a therapeutically effective amount of a muscarinic receptor agonist comprising m1 receptor agonist activity, and more preferably m1 selective agonist activity. Although any known m1 receptor selective agonist may be used in practicing the invention, preferably the compounds of the present invention as described herein are used. Exemplary agonists available in the art include xanomeline (3-[4-(hexyloxy)-1,2,5-thiadiazol-3-yl]-1,2,5,6-tetrahydro-1-methylpyridine) (Novo Nordisk); talsaclidine (3-(2-propynyloxy)-1-azabicyclo[2,2,2]octane)(Boehringer Ingelheim); Z-1- azabicyclo[2.2.1]heptane-3-one, O-[3-(3-methoxyphenyl)-2-propynyl]oxime (Parke-Davis PD-151832); sabcomeline (R-(Z)-α-(methoxyimino)-1-azabicyclo-[2,2,2]octane-3-acetonitrile HCl)(SmithKline Beecham); 2,8-dimethyl-3-methylene-1-oxa-8-azaspiro[4.5]decane (Yamanouchi Pharmaceutical Co. YM-796); WAY-132983 (Wyeth-Ayerst Research); cevimeline (2'-methyl-spiro[1-azabicyclo[2,2,2] octane-3,5'-[1,3]oxathiolane] (Snow Brand Milk Products Co); alvameline (5-(2-ethyl-2H-tetrazol-5-yl)-1,2,3,6-tetrahydro-1-methyl-pyridine)(H Lundbeck A/S); milameline (1,2,5,6-tetrahydro-1-methyl-3-pyridinecarboxaldehyde, O-Ego methyloxime)(Parke-Davis & Co); and those described in, for example, U.S. Pat. Nos. 5,175,166, 5,403,845, 5,534,522, 4,992,457, 5,571,819, 5,093,333, 5,468,875, 5,510,478, 5,756,501, 5,834,458, EP 384288, WO 9917771, JP 61280497, WO 9700894, WO 9847900, WO 9314089, EP 805153, WO 9422861, WO 9603377, EP 429344, EP 647642, WO 9626196, WO 9800412, WO 9531457, JP 61280497, JP 6298732, JP 6305967, WO 9640687, EP 311313, EP 370415, EP 709381, EP 723781, EP 727208, EP 727209, WO 9740044 and EP 384285, all of which are incorporated herein by reference.

The compounds of the present invention preferably show selective agonist activity towards the m1 receptor. Such an agonist is defined as a compound that increases the activity of the m1 muscarinic receptor when it contacts the receptor. With respect to the m1 receptor, selectivity means that an agonist causes a relatively greater increase in the activity of the m1 receptor than of the m3 receptor subtype. Preferably, the agonist causes at least about a 10 fold greater increase in activity of the m1 receptor than of the m3 receptor. Preferably, the m1 selective agonist also causes a relatively greater increase, preferably at least about a 10 fold greater increase, in the activity of an m1 receptor than of an m2; preferably than of an m4; and preferably than of an m5. In one embodiment, selectivity is defined as a property of a muscarinic m1 agonist whereby an amount of agonist effective to increase the activity of the m1 receptor causes little or no increase in the activity of the m3 and m5 subtypes, and preferably the m2 and m4 subtypes.

As used herein, the term "alkyl" means a straight or branched-chain alkane group with 1–6 carbon atoms in the chain, for instance methyl, ethyl, propyl, isopropyl, n-butyl, sec-butyl, tert-butyl, etc. The term "heteroalkyl" is intended to indicate an alkane group containing 1 or 2 heteroatoms selected from O, S or N.

As used herein, the term "alkenyl" means a straight or branched-chain alkene group with 2–6 carbon atoms in the chain; the term "alkynyl" is intended to indicate a straight or is branched-chain alkyne group with 2–6 carbon atoms in the chain.

As used herein, the terms "aryl" and "cycloalkyl" preferably refer to mono- and bicyclic ring structures comprising 5 to 12 carbon atoms, more preferably monocyclic rings comprising 5 to 6 carbon atoms. Where such rings comprise one or more heteroatoms, selected from N, S and O, (i.e., heterocyclic rings) such rings comprise a total of 5 to 12 atoms, more preferably 5 to 6 atoms. Heterocyclic rings include, but are not limited to, furyl, pyrrolyl, pyrazolyl, thienyl, imidazolyl, isoxazolyl, oxazolyl, thiazolyl, isothiazolyl, pyridyl, piperidinyl, piperazinyl, pyridazinyl, pyrimidinyl, pyrazinyl, morpholinyl, oxadiazolyl, thiadiazolyl, imidazolinyl, imidazolidinyl and the like. The ring may be substituted by one or more of the groups included in the definition of $R_2$ above. It is understood that the substituents $C_{1-6}$ alkyl, $C_{1-6}$ alkenyl, $C_{1-6}$ alkynyl, $C_{1-6}$ alkoxy, $C_{1-6}$ heteroalkyl, $C_{1-6}$ aminoalkyl, $C_{1-6}$ haloalkyl or $C_{1-6}$ alkoxycarbonyl may, if present, be substituted by one or more of hydroxyl, $C_{1-4}$ alkoxy, halogen, cyano, amino or nitro.

As used herein, the term "halogen" or "halo" includes chlorine, fluorine, iodine and bromine.

It is understood that the ring represented by the structure

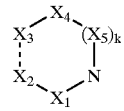

may be both saturated and unsaturated.

Compounds of the present invention may be prepared by methods analogous to the methods disclosed in GB 1,142, 143 and U.S. Pat. No. 3,816,433. Ways of modifying those methods to include other reagents etc. will be apparent to those skilled in the art. Thus, for instance, compounds of formula I may be prepared as shown in the following reaction scheme.

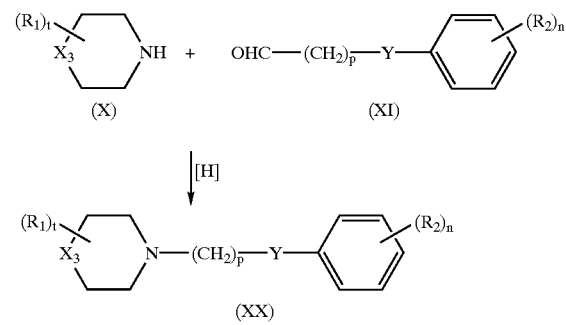

The starting compound having formula (X) may be prepared by general methods of organic synthesis. For general methods of preparing compounds of formula (X), reference is made to Fuller, R. W. et al., *J. Med. Chem.* 14:322–325 (1971); Foye, W. O., et al., *J. Pharm. Sci.* 68:591–595 (1979); Bossier, J. R. et al., *Chem. Abstr.* 66:46195h and 67:21527a (1967); Aldous, F. A. B., *J. Med. Chem.* 17:1100–1111 (1974); Fuller, R. W. et al., *J. Pharm. Pharmacol.* 25:828–829 (1973); Fuller, R. W. et al., *Neuropharmacology* 14:739–746 (1975); Conde, S. et al., *J. Med. Chem.* 21:978–981 (1978); Lukovits, I. et al., *Int. J. Quantum Chem.* 20:429–438 (1981); and Law, B., *J. Cromatog.* 407:1–18 (1987), the disclosures of which are incorporated by reference herein in their entirety. The radiolabelled derivatives having formula (XX) may be prepared by, for example, using a tritiated reducing agent to form the reductive amination or by utilizing a $^{14}C$-labelled starting material.

Alternatively, where the starting compound comprises a carbonyl group, the compound having the formula (XXII) may be reduced with, for example, $AlH_3$, diborane:methyl sulfide or other standard carbonyl reducing reagents to produce the ligand having the formula (XXX).

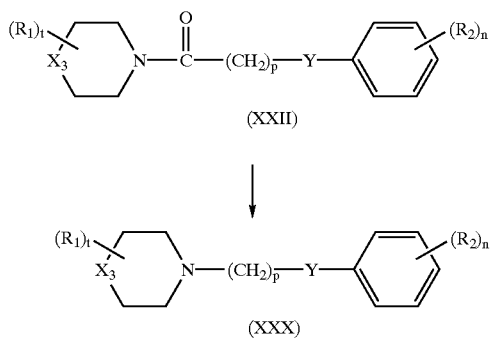

(XXII)

↓

(XXX)

The receptor ligands having formula (XXXII) may be prepared by nucleophilic displacement of an electrophile (E) by the amino derivative (XXXI). Examples of electrophiles which may be used for this purpose include halides such as I, Cl, Br, tosylate or mesylate.

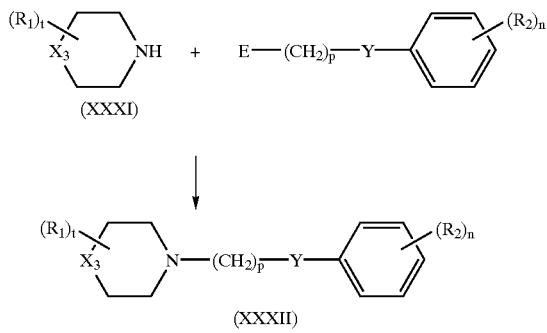

When Y in formula (XXXII) is —C(O)—, this compound may be prepared from oxidation of an sec. alcohol with for example pyridinium chlorocromate or N-chlorosuccinimide or $CrO_3$—$H_2SO_4$ or nickel peroxide or metal (Al, K) or DCC-DMSO.

When Y in formula (XXXII) is —O—, this compound may be prepared by alkylation of an alcohol with arylhalides under for example Cu catalysis.

When Y in formula (XXXII) is —S—, this compound may be prepared by alkylation of a thiol with arylhalides under for example Cu catalysis.

When Y in formula (XXXII) is —CHOH—, this compound may be prepared by reduction of the corresponding ketone by catalytic hydrogenation or by the use of $NaBH_4$ or by the use of $LiAlH_4$.

Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quarternary ammonium salts. Examples of pharmaceutically acceptable salts include the acetate, benzenesulfonate, benzoate, bicarbonate, bisulfate, bitartrate, borate, bromide, calcium, carbonate, chloride, clavulanate, citrate, dihydrochloride, fiunarate, gluconate, glutamate, hydrobromide, hydrochloride, hydroxynaphthoate, iodide, isothionate, lactate, lactobionate, laurate, maleate, mandelate, mesylate, methylbromide, methylnitrate, methylsulfate, nitrate, N-methylglucamine ammonium salt, oleate, oxalate, phosphate/diphosphate, salicylate, stearate, sulfate, succinate, tannate, tartrate, tosylate, triethiodide and valerate salt.

The present invention includes within its scope prodrugs of the compounds of this invention. In general, such prodrugs are inactive derivatives of the compounds of this invention which are readily convertible in vivo into the required compound. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

Where the compounds according to the invention have at least one chiral center, they may exist as a racemate or as enahtiomers. It should be noted that all such isomers and mixtures thereof are included in the scope of the present invention. Furthermore, some of the crystalline forms for compounds of the present invention may exist as polymorphs and as such are intended to be included in the present invention. In addition, some of the compounds of the present invention may form solvates with water (i.e., hydrates) or common organic solvents. Such solvates are also included in the scope of this invention.

Where the processes for the preparation of the compounds according to the invention give rise to mixtures of stereoisomers, such isomers may be separated by conventional techniques such as preparative chiral chromatography. The compounds may be prepared in racemic form, or individual enantiomers may be prepared either by stereoselective synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

Compounds of the present invention may be administered in any of the foregoing compositions and according to dosage regimens established in the art whenever specific pharmacological modification of the activity of muscarinic receptors is required.

The present invention also provides pharmaceutical compositions comprising one or more compounds of the invention together with a pharmaceutically acceptable diluent or excipient. Preferably such compositions are in unit dosage forms such as tablets, pills, capsules (including sustained-release or delayed-release formulations), powders, granules, elixirs, tinctures, syrups and emulsions, sterile parenteral solutions or suspensions, aerosol or liquid sprays, drops, ampoules, auto-injector devices or suppositories; for oral, parenteral (e.g. intravenous, intramuscular or subcutaneous), intranasal, sublingual or rectal administration, or for administration by inhalation or insufflation, and may be formulated in an appropriate manner and in accordance with accepted practices such as those disclosed in *Remington's Pharmaceutical Sciences*, Gennaro, Ed., Mack Publishing Co., Easton Pa., 1990. Alternatively, the compositions may be in sustained-release form suitable for once-weekly or once-monthly administration; for example, an insoluble salt of the active compound, such as the decanoate salt, may be adapted to provide a depot preparation for intramuscular injection. The present invention also contemplates providing suitable topical formulations for administration to, e.g. eye or skin or mucosa.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents, flavoring agents and coloring agents can also be incorporated into the mixture. Suitable binders include, without limitation, starch, gelatin, natural sugars such as glucose or beta-lactose, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

For preparing solid compositions such as tablets, the active ingredient is mixed with a suitable pharmaceutical excipient, e.g. such as the ones described above, and other pharmaceutical diluents, e.g. water, to form a solid preformulation composition containing a homogeneous mixture of a compound of the present invention, or a pharmaceutically acceptable salt thereof. By the term "homogeneous" is meant that the active ingredient is dispersed evenly throughout the composition so that the composition may be readily subdivided into equally effective unit dosage forms such as tablets, pills and capsules. The solid preformulation composition may then be subdivided into unit dosage forms of the type described above containing from 0.1 to about 50 mg of the active ingredient of the present invention. The tablets or pills of the present composition may be coated or otherwise compounded to provide a dosage form affording the advantage of prolonged action. For example, the tablet or pill can comprise an inner core containing the active compound and an outer layer as a coating surrounding the core. The outer coating may be an enteric layer which serves to resist disintegration in the stomach and permits the inner core to pass intact into the duodenum or to be delayed in release. A variety of materials can be used for such enteric layers or coatings, such materials including a number of polymeric acids and mixtures of polymeric acids with conventional materials such as shellac, cetyl alcohol and cellulose acetate.

The liquid forms in which the present compositions may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical carriers. Suitable dispersing or suspending agents for aqueous suspensions include synthetic and natural gums such as tragacanth, acacia, alginate, dextran, sodium carboxymethylcellulose, gelatin, methylcellulose or polyvinyl-pyrrolidone. Other dispersing agents which may be employed include glycerin and the like. For parenteral administration, sterile suspensions and solutions are desired. Isotonic preparations which generally contain suitable preservatives are employed when intravenous administration is desired. The compositions can also be formulated as an ophthalmic solution or suspension formation, i.e., eye drops, for ocular administration.

Consequently, the present invention also relates to a method of alleviating or treating a disease or condition in which modification of muscarinic receptor activity, in particular m1 receptor activity, has a beneficial effect by administering a therapeutically effective amount of a compound of the present invention to a subject in need of such treatment. Such diseases or conditions may, for instance arise from inadequate stimulation or activation of muscarinic receptors. It is anticipated that by using compounds which are selective for a particular muscarinic receptor subtype, in particular m1, the problems with adverse side effects observed with the known muscarinic drugs, such as tachycardia or bradycardia or gastrointestinal effects, may substantially he avoided.

The term "subject," as used herein refers to an animal, preferably a mammal, most preferably a human, who has been the object of treatment, observation or experiment.

The term "therapeutically effective amount" as used herein means that amount of active compound or pharmaceutical agent that elicits the biological or medicinal response in a tissue, system, animal or human that is being sought by a researcher, veterinarian, medical doctor or other clinician, which includes alleviation of the symptoms of the disease being treated.

Preferably, compounds of general formula I exhibit subtype selectivity for the muscarinic m1 receptor subtype. Likewise, the compounds exhibit selectivity for the muscarinic m1 receptor subtype compared to other human G-protein coupled receptors tested including serotonin, histamine, dopamine or adrenergic receptors. One important implication of this selectivity is that these compounds may be effective in the treatment or amelioration of a number of diseases and disorders of the central nervous system without the undesirable side effects previously observed with non-selective compounds.

The ability of the compounds of the present invention to demonstrate muscarinic m1 receptor subtype selectivity makes them potentially very useful in treating a number of diseases and disorders characterized by cognitive impairment such as attention deficit disorder, or neurodegenerative diseases, e.g. Alzheimer's disease, other forms of age-related cognitive decline, e.g. senile dementia, or dementia-related symptoms such as decreased motor activity, mood changes, anergia, apathy, restlessness and aggressive behavior. It is currently believed that the muscarinic m1 receptor may also be involved in control of intraocular pressure, and that muscarinic m1 agonists may therefore be used to treat or alleviate ocular diseases such as glaucoma.

Advantageously, compounds of the present invention may be administered in a single daily dose, or the total daily dosage may be administered in divided doses two, three or four times daily. Furthermore, compounds for the present invention may be administered in intranasal form via topical use of suitable intranasal vehicles, or via transdermal routes, using those forms of transdermal skin patches well known to persons skilled in the art. To be administered in the form of a transdermal delivery system, the dosage administration will, of course, be continuous rather than intermittent throughout the dosage regimen.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound employed. A physician or veterinarian of ordinary skill can readily determine and prescribe the effective amount of the drug required to prevent, counter or arrest the progress of the disease or disorder which is being treated.

The daily dosage of the products may be varied over a wide range from 0.01 to 100 mg per adult human per day. For oral administration, the compositions are preferably provided in the form of tablets containing 0.01, 0.05, 0.1, 0.5, 1.0, 2.5, 5.0, 10.0, 15.0, 25.0 or 50.0 mg of the active ingredient for the symptomatic adjustment of the dosage to the patient to be treated. A unit dose typically contains from about 0.001 mg to about 50 mg of the active ingredient, preferably from about 1 mg to about 10 mg of active ingredient. An effective amount of the drug is ordinarily supplied at a dosage level of from about 0.0001 mg/kg to about 25 mg/kg of body weight per day. Preferably, the range is from about 0.001 to 10 mg/kg of body weight per day, and especially from about 0.001 mg/kg to 1 mg/kg of body weight per day. The compounds may be administered on a regimen of 1 to 4 times per day.

Compounds according to the present invention may be used alone at appropriate dosages defined by routine testing in order to obtain optimal pharmacological effect on a muscarinic receptor, in particular the muscarinic m1 receptor subtype, while minimizing any potential toxic or otherwise unwanted effects. In addition, co-administration or sequential administration of other agents which improve the effect of the compound may, in some cases, be desirable.

The pharmacological properties and the selectivity of the compounds of this invention for specific muscarinic receptor subtypes may be demonstrated by a number of different assay methods using recombinant receptor subtypes, preferably of the human receptors if these are available, e.g. conventional second messenger or binding assays. A particularly convenient finctional assay system is the receptor selection and amplification assay disclosed in U.S. Pat. No. 5,707,798 describing a method of screening for bioactive compounds by utilizing the ability of cells transfected with receptor DNA, e.g. coding for the different muscarinic subtypes, to amplify in the presence of a ligand of the receptor. Cell amplification is detected as increased levels of a marker also expressed by the cells.

The invention is disclosed in further detail in the following examples which are not in any way intended to limit the scope of the invention as claimed.

EXAMPLES

Example I 4-n-Butyl-1-[4-(2-methylphenyl)-4-oxo-1-butyl]piperidine (5)

1-Benzyl-4-n-butylidenepiperidine (2). A 500 mL 3-necked flask fitted with a stirrer, was charged with sodium hydride (1.61 g, 67 mmol) and DMSO (40 mL). The resulting suspension was heated to 90° C. for 30 min, until the evolution of hydrogen ceased. The suspension was cooled on an ice-bath for 20 min followed by addition of a slurry of butyltriphenylphosphonium bromide (26.6 g, 67 mmol) in DMSO (70 mL). The red mixture was stirred for 15 min at rt. 1-Benzyl-4-piperidone 1 (14.0 g, 74 mmol) was slowly added over 30 min, and the mixture was stirred at room temperature over night. $H_2O$ (200 mL) was added to the reaction mixture followed by extraction with heptane (4×100 mL) and ethyl acetate (2×100 mL). The combined organic phases were dried and evaporated to dryness, producing 38.1 g of a yellow oil. The oil was distilled to give 14.9 g (88%) of 2, bp 101–105° C. (0.1 mm Hg). $^1$H NMR (CDCl$_3$) δ 0.90–0.95 (t, 3H), 1.25–1.41 (m, 2H), 1.90–2.20 (m, 2H), 2.18–2.30 (m, 4H), 2.40–2.45 (m, 4H), 2.50 (s, 2H), 5.17 (t, 1H), 7.20–7.42 (m, 5H).

4-n-Butylpiperidine (3). In a 500 mL flask fitted with a stirrer was added a slurry of 2 (13.2 g, 58 mmol) and 10% palladium on charcoal (1.2 g) in ethanol (70 mL), followed by addition of concentrated hydrochloric acid (1.5 mL). The reaction flask was evacuated and hydrogen was added via a reaction flask. A total of 2.5 dm$^3$ of hydrogen was consumed. The reaction mixture was filtered and evaporated and the residue was dissolved in $H_2O$ (40 mL) and NaOH (20 mL, 2 M) followed by extraction with ethyl acetate (3×100 mL). The combined organic phases were washed with brine (30 mL) and evaporated to dryness to produce 7.1 g of crude 3. The crude product was subjected to CC [eluent:heptane:EtOAc (4:1)] to give pure 3 (2.7 g, 33%). $^1$H NMR (CDCl$_3$) δ 0.85 (t, 3H), 1.0–1.38 (m, 9H), 1.65 (dd, 2H), 2.38 (s, 1H), 2.55 (dt, 2H), 3.04 (dt, 2H).

4-(4-n-Butylpiperidin-1-yl)butanenitrile (4). In a 100 mL flask with a magnetic stirrer was placed 3 (2.3 g, 16.4 mmol), 4-bromobutyronitrile (2.4 g, 16.4 mmol), potassium carbonate powder (2.5 g, 18 mmol) in acetonitrile (20 mL). The reaction mixture was stirred at rt for 5 h followed by addition of $H_2O$ (15 mL). The mixture was extracted with ethyl acetate (3×30 mL) and the combined organic phases were evaporated to dryness to produce 3.9 of crude 4. The crude product was subjected to CC [eluent: heptane: EtOAc (1:1)] to give pure 4 (2.3 g, 87%). $^1$H NMR (CDCl$_3$) δ 0.82 (t, 3H), 1.19–1.37 (m, 9H), 1.64–1.75 (d, 2H), 1.84–2.01 (m, 4H), 2.39–2.54 (m, 4H), 2.89–2.97 (d, 2H).

4-n-Butyl-1-[4-(2-methylphenyl)-4-oxo-1-butyl] piperidine (5). In a 25 mL oven-dried flask was charged Mg turnings (125 mg, 5.2 mmol) which were activated by the use of a heat-gun. Under inert atmosphere was added a suspension of 2-iodoanisole (1.13 g, 5.2 rmmol) in $Et_2O$ (4 mL) and the reaction mixture was allowed to stand at rt for 1 hour. Compound 4 (720 mg, 3.4 mmol) dissolved in $Et_2O$ (4 mL) was added and the mixture was refluxed over-night. THF (15 mL) and sulfuric acid (4 mL, 2 M) was added and the reaction mixture was stirred for 4 h, followed by addition of NaOH (6 mL, 2 M). The reaction mixture was extracted with ethyl acetate (3×50 mL), and the combined organic phases were evaporated to dryness to produce 1.2 g of crude 5. The crude product was subjected to CC [eluent: $CH_2Cl_2$:$CH_3OH$ (99:1)] to give pure 5 (0.42 g, 26%). $^1$H NMR (CDCl$_3$) δ 0.83 (t, 3H), 1.20–1.42 (m, 9H), 1.65–1.73 (d, 2H), 1.96–2.20 (m, 4H), 2.53 (t, 2H), 3.02–3.17 (m, 4H), 3.89 (s, 3H), 6.95–7.01 (m, 2H), 7.44 (t, 1H), 7.65 (d, 1H).

Example II

3-Hydroxymethyl-1-[4-(2-methylphenyl)-4-oxo-1-butyl]piperidine (7)

4-(3-Hydroxymethyl-piperidin-1-yl)-butyronitrile (6). In an oven-dried 25 mL flask was placed piperidine-3-yl-methanol (1.12 g, 10 mmol) in acetonitrile (10 mL), followed by addition of potassium carbonate (1.38 g, 10 mmol) and 4-bromobutyronitrile (0.90 mL, 9 mmol). The reaction mixture was stirred at rt. for 12 h. The mixture was filtered and evaporated to dryness. Addition of H$_2$O (20 mL) was followed by extraction with ethyl acetate (3×20 mL) and the combined organic phases were dried (MgSO$_4$) and evaporated to dryness to produce 1.50 g of crude 6 which was used without further purification in the synthesis of compound 7.

3-Hydroxymethyl-[4-(2-methylphenyl)-4-oxo-1-butyl] piperidine (7). In a 50 mL oven-dried flask was added Mg turnings (780 mg, 32 mmol), which were activated by the use of a heat-gun under vacuum, followed by addition of anhydrous THF (7 mL). Under inert atmosphere was added a suspension of 2-iodotoluene (5.3 g, 24 mmol) in THF (10 mL) and the reaction mixture was allowed to reflux for 4 hours. A suspension of compound 6 (1.50 g, 8 mmol) in THF (5 mL) was added via a syringe followed by addition of CuBr (23 mg, 0.16 mmol, 2 mol %) and the reaction mixture was stirred at rt overnight. The reaction mixture was quenched by addition of H$_2$SO$_4$ (20 mL, 2 M) and stirred at rt for 2 hours followed by addition of NaOH (8 mL, 2 M). Addition of THF (15 mL) was followed by extraction with CH$_2$Cl$_2$ (3×20 mL), and the organic phases were dried (MgSO$_4$) and evaporated to dryness to produce 0.41 g of crude 7. The crude product was subjected to preparative HPLC CC [eluent: Buffer A: 0.1% TFA; Buffer B: 80% CH$_3$CN+0.1% TFA] to produce an analytical pure sample of compound 7. LC-MS [M+H]$^+$275 (cald. 275.2).

Example III

2-Propyl-[4-(2-methylphenyl)-4-oxo-1-butyl] piperidine (9)

4-(2-propyl-piperidin-1-yl)-butyronitrile (8). A mixture of 2-propylpiperidine (550 mg, 4.3 mmol), 4-bromobutyronitrile (430 mg, 3.0 mmol) and potassium carbonate (550 mg, 4.0 mmol) in acetonitrile (5 mL) was stirred at rt for 12 h., followed by addition of a saturated brine (25 mL). The reaction mixture was extracted with ethyl acetate (3×25 mL) and the combined organic phases were dried (MgSO$_4$) and evaporated to dryness to produce crude 8. The crude product was subjected to CC [eluent: CH$_2$Cl$_2$: MeOH (99: 1)] to give pure 8 (0.48 g, 83%); LC-MS [M+H]$^+$194 (cald. 194.2).

2-Propyl-[4-(2-methylphenyl)-4-oxo-1-butyl]piperidine (9). In a 10 mL oven-dried flask was added Mg turnings (97 mg, 4.1 mmol) which were activated by the use of a heat-gun under vacuum. Under inert atmosphere was added a suspension of 2-iodotoluene (380 μl, 2.8 mmol) in Et$_2$O (3 mL) and the reaction mixture was allowed to reflux for 1 hour. A mixture of compound 8 (0.43 g, 2.2 mmol) in CH$_2$Cl$_2$ (3 mL) was added via a syringe and the reaction mixture was stirred at rt overnight. The reaction mixture was quenched by addition of H$_2$SO$_4$ (10 mL, 2 M) and stirred at rt for 12 hours followed by addition of NaOH (10 mL, 2 M). Addition of THF (15 mL) was followed by extraction with ethyl acetate (3×50 mL) and the combined organic phases are washed with brine (10 mL) and NaOH (10 mL, 2 M), dried (MgSO$_4$) and evaporated to dryness to produce 0.43 g of crude 9. The crude product was subjected to preparative HPLC [eluent: Buffer A: 0.1% TFA; Buffer B: 80% CH$_3$CN+0.1% TFA] to produce an analytically pure sample of compound 9; LC-MS [M+H]$^+$287 (cald. 287.2).

Example IV

1-[4-(2-Methylphenyt)-4-oxo-1-butyl]piperidine (11)

In a 10 mL oven-dried flask was added Mg turnings (97 mg, 4.1 mmol) which was activated by the use of a heat-gun under vacuum. Under inert atmosphere was added a suspension of 2-iodo-toluene (380 μL, 3.0 mmol) in Et$_2$O (3 mL) and the reaction mixture was allowed to reflux for 1 hours. A suspension of 4-piperidin-1-yl-butanenitrile 10 (Dahlbom et. al. Acta. Chem. Scand. 1951, 5, 690–697) (0.305 mg, 2.0 mmol) in CH$_2$Cl$_2$ (3 mL) was added via a syringe and the reaction mixture was stirred at rt overnight. The reaction mixture was quenched by addition of H$_2$SO$_4$ (10 mL, 2 M) and stirred at rt for 12 hours followed by addition of NaOH (12 mL, 2 M). Addition of THF (15 mL) was followed by extraction with ethyl acetate (3×50 mL), and the combined organic phases are washed with brine (10 mL) and NaOH (10 mL, 2 M), and dried (MgSO$_4$) and evaporated to dryness to produce 0.21 g of crude 11. The crude product was subjected to preparative HPLC [eluent: Buffer A: 0.1% TFA; Buffer B: 80% CH$_3$CN+0.1% TFA] to produce an analytically pure sample of compound 11; LC-MS [M+H]$^+$245 (cald. 245.2).

Example V

4-Methyl-1-[4-(4-bromophenyl)-4-oxo-1-butyl] piperidine (12)

In a 10 mL dried flask was, added 4-methylpiperidine (719 μL, 6 mmol), dioxane (5 mL) followed by addition of potassium carbonate (0.30 g, 2.18 mmol), potassium iodide (10 mg) and 4-bromo-4-chlorobutyrophenone (785 mg, 2.76 mmol). The reaction mixture was left at 110° C. for 12 h., followed by dilution with H$_2$O (10 mL). The reaction mixture was extracted with Et$_2$O (3×15 mL) and the combined organic phases are dried (MgSO$_4$) and evaporated to dryness to produce 0.50 g of crude 12. The crude product was subjected to preparative HPLC [eluent: Buffer A: 0.1% TFA; Buffer B: 80% CH$_3$CN+0.1% TFA] to produce an analytical pure sample of compound 12; LC-MS [M+H]$^+$ 322 (cald. 323.1).

Example VI

1-[4-(2-Methylphenyl)4-oxo-1-butyl]pyrrolidine (13)

In a 10 mL oven-dried flask was charged Mg turnings (30 mg, 1.2 mmol) which were activated under vacuum by the use of a heat-gun. Under inert atmosphere was added a solution of 2-iodotoluene (0.22 g, 1.0 mmol) in Et$_2$O (2 mL) and the reaction mixture was allowed to reflux for 1 hour. A mixture of 4-pyrrolidin-1-yl-butyronitrile (Burckhalter et. al. J. Org. Chem. 1961, 26, 4070–4076) (0.14 g, 1.0 mmol) in CH$_2$Cl$_2$ (2 mL) was added via a syringe and the reaction mixture was stirred at rt overnight. The reaction mixture was quenched by addition of H$_2$SO$_4$ (10 mL, 2 M) and stirred at rt for 2 hours followed by addition of NaOH (10 mL, 2 M). Addition of THF (15 mL) was followed by extraction with ethyl acetate (3×20 mL), and the organic phases were dried (MgSO$_4$) and evaporated to dryness to produce 0.12 g of crude 13. The crude product was subjected to preparative HPLC [eluent: Buffer A: 0.1% TFA; Buffer B: 80% CH$_3$CN+0.1% TFA] to produce an analytical pure sample of compound 13. LC-MS [M+H]$^+$ 231 (cald. 231.3).

Example VII

4-Methyl-1-[4-(2-methylphenyl)4-oxo-1-butyl] piperazine (15)

4-(4-Methyl-piperazin-1-yl)-butyronitrile (14). In a 25 mL flask was placed 1-methyl-piperazine (0.52 g, 5.1 mmol), 4-bromobutyronitrile (0.78 g, 5.3 mmol) and potassium carbonate (0.71 g, 5.3 mmol) suspended in acetonitrile (5 mL). The reaction mixture was stirred at rt for 4 h., followed by addition of $H_2O$ (20 mL) and extraction with ethyl acetate (3×25 mL). The combined organic phases were washed with brine (25 mL), dried ($MgSO_4$) and evaporated to dryness to produce 0.72 g of crude 14 which was used without further purification in the synthesis of compound 15.

4-Methyl-1-[4-(2-methylphenyl)4-oxo-1-butyl]piperazine (15). In a 10 mL oven-dried flask was added Mg turnings (116 mg, 4.0 mmol) which were activated under vacuum by the use of a heat-gun. Under inert atmosphere was added a mixture of 2-iodotoluene (0.65 g, 3.0 mmol) in $Et_2O$ (3 mL) and the reaction mixture was allowed to reflux for 1 hour. A solution of compound 14 (0.33 g, 2.0 mmol) in $CH_2Cl_2$ (3 mL) was added via a syringe and the reaction mixture was stirred at rt overnight. The reaction mixture was quenched by addition of $H_2SO_4$ (6 mL, 2 M) and stirred at rt for 2 hours followed by addition of NaOH (8 mL, 2 M). Addition of THF (15 mL) was followed by extraction with $CH_2Cl_2$ (3×20 mL). The organic phases were dried ($MgSO_4$) and evaporated to dryness to produce 0.26 g of crude 15. The crude product was subjected to preparative HPLC [eluent: Buffer A: 0.1% TFA; Buffer B: 80% $CH_3CN$+0.1% TFA] to produce an analytically pure sample of compound 15. LC-MS $[M+H]^+$ 260 (cald. 260.4).

Example VIII 4-n-Butyl-1-[4-(2-methylphenyl)4-oxo-1-butyl]piperazine (17)

4-(4-Butyl-piperazin-1-yl)-butyronitrile (16). In a 25 mL flask was placed 1-butyl-piperazine (712 mg, 5.0 mmol), 4-bromobutyronitrile (779 mg, 5.3 mmol) and potassium carbonate (687 mg, 5.0 mmol) suspended in acetonitrile (5 mL). The reaction mixture was stirred at rt for 12 h., followed by addition of $H_2O$ (20 mL) and extraction with ethyl acetate (3×25 mL). The combined organic phases were washed with brine (25 mL), dried ($MgSO_4$) and evaporated to dryness to produce 0.89 g of crude 16 which was used without further purification in the synthesis of compound 17.

4-n-Butyl-1-[4-(2-methylphenyl)4-oxo-1-butyl]piperazine (17). In a 10 mL oven-dried flask charged with Mg turnings (100 mg, 4.0 mmol) which was activated under vacuum by the use of a heat-gun. Under inert atmosphere was added a suspension of 2-iodotoluene (0.66 g, 3.0 mmol) in $Et_2O$ (3 mL) and the reaction mixture was allowed to reflux for 1 hours. A suspension of compound 16 (0.43 g, 2.0 mmol) in $CH_2Cl_2$ (3 mL) was added via a syringe and the reaction mixture was stirred at rt overnight. The reaction mixture was quenched by addition of $H_2SO_4$ (6 mL, 2 M) and stirred at rt for 2 hours followed by addition of NaOH (8 mL, 2 M). Addition of THF (15 mL) was followed by extraction with $CH_2Cl_2$ (3×20 mL), and the organic phases were dried ($MgSO_4$) and evaporated to dryness to produce 0.50 g of crude 17. The crude product was subjected to preparative HPLC [eluent:,Buffer A: 0.1% TFA; Buffer B: 80% $CH_3CN$+0.1% TFA] to produce an analytical pure sample of compound 17. LC-MS $[M+H]^+$ 302 (cald. 302.5).

Example IX 4-n-Butyl-1-[4-(2-ethoxyphenyl)-4-oxo-1-butyl]piperidine (18)

In a 10 mL oven-dried flask was added Mg turnings (94 mg, 3.8 mmol) which was activated by the use of a heat-gun under vacuum. Under inert atmosphere was added a suspension of 1-ethoxy-2-iodobenzene (0.71 g, 2.9 mmol) in $Et_2O$ (3 mL) and the reaction mixture was allowed to reflux for 3 hours. Compound 4 (0.40 g, 1.9 mmol) dissolved in $CH_2Cl_2$ (3 mL) was added and the mixture was stirred at 40° C. for additional 3 hours. The reaction mixture was quenched by addition of $H_2SO_4$ (10 mL, 2 M) and left stirring overnight at room temperature, followed by addition of NaOH (20 mL, 2 M) until basic conditions. The reaction mixture was extrated with ethyl acetate (3×50 mL) ) and the combined organic phases are washed with brine (10 mL) and NaOH (10 mL, 2 M), and the combined organic phases were dried ($MgSO_4$) and evaporated to dryness to produce 0.60 g of crude 18. The crude product was subjected to CC [eluent:Tol:EtOAc (1:1)] to give pure 18 (0.32 g, 34%); LC-MS $[M+H]^+$ 331 (cald. 331.5).

Example X 4-n-Butyl-1-[4-(2,3-dimethylphenyl)-4-oxo-1-butyl]piperidine (19)

In a 10 mL oven-dried flask was added Mg turnings (94 mg, 3.8 mmol) which was activated under vacuum by the use of a heat-gun. Under inert atmosphere was added a suspension of 1-iodo-2,3-dimethylbenzene (0.69 g, 3.0 mmol) in $Et_2O$ (5 mL) under spontaneously reflux, and the reaction mixture was allowed to reflux for 4 hours. A suspension of compound 4 (0.41 g, 2.0 mmol) in $CH_2Cl_2$ (2 mL) was added to the reaction mixture and left at rt overnight. The reaction mixture was quenched by addition of $H_2SO_4$ (7 mL, 2 M) and stirred at rt for 3 hours, followed by addition of NaOH (20 mL, 2 M) until basic conditions. The reaction mixture was extracted with ethyl acetate (3×50 mL) and the combined organic phases are washed with brine (10 mL) and NaOH (10 mL, 2 M), and the organic phases were dried ($MgSO_4$) and evaporated to dryness to produce 0.69 g of crude 19. The crude product was subjected to CC [eluent: $CH_2Cl_2$: MeOH (99:1)] to give pure 19 (0.40 g, 64%); LC-MS $[M+H]^+$ 315 (cald. 315.5).

Example XI 4-n-Butyl-1-[4-(2,4-dimethylphenyl)-4-oxo-1-butyl]piperidine (20)

In a 10 mL oven-dried flask charged with Mg turnings (95 mg, 3.9 mmol) which was activated under vacuum by the use of a heat-gun. Under inert atmosphere was added a suspension of 1-iodo-2,4-dimethylbenzene (0.69 g, 2.9 mmol) in $Et_2O$ (4.5 mL) under spontaneously reflux, and the reaction mixture was allowed to reflux for 3 hours. Compound 4 (0.41 g, 2.0 mmol) dissolved in $CH_2Cl_2$ (2 mL) was added under inert atmosphere to the reaction mixture and left stirring at rt overnight. The reaction mixture was quenched by addition of $H_2SO_4$ (8 mL, 2 M) and stirred at rt for 4 hours, then the reaction mixture was basified by addition of NaOH (20 mL, 2 M). Addition of THF (20 mL) was followed by extraction with ethyl acetate (3×50 mL) and the combined organic phases are washed with brine (10 mL) and NaOH (10 mL, 2 M), and the organic phases were dried ($MgSO_4$) and evaporated to dryness to produce 0.61 g of crude 20. The crude product was subjected to CC [eluent: $CH_2Cl_2$:MeOH (99:1)] to give pure 20 (0.21 g, 35%); LC-MS $[M+H]^+$ 315 (cald. 315.5).

Example XII 4-n-Butyl-1-[4-(2-ethyylphenyl)-4-oxo-1-butyl]piperidine (21).

In a 10 mL oven-dried flask charged with Mg turnings (0.12 g, 4.9 mmol) which was activated under vacuum by the use of a heat-gun. Under inert atmosphere was added a suspension of 1-bromo-2-ethylbenzene (0.66 g, 3.6 mmol) in Et$_2$O (2 mL) and the reaction mixture was allowed to reflux for 2 hours. A suspension of compound 4 (0.50 g, 2.4 mmol) in CH$_2$Cl$_2$ (2 mL) was added via a syringe and the reaction mixture was stirred at rt overnight. The reaction mixture was quenched by addition of H$_2$SO$_4$ (14 mL, 2 M) and stirred at rt for 2 hours followed by addition of NaOH (20 mL, 2 M). Addition of THF (20 mL) was followed by extraction with ethyl acetate (3×50 mL) and the combined organic phases are washed with brine (10 mL) and NaOH (10 mL, 2 M), and the organic phases were dried (MgSO$_4$) and evaporated to dryness to produce 0.75 g of crude 21. The crude product was subjected to CC [eluent:CH$_2$Cl$_2$:MeOH (99:1)] to give pure 21 (0.68 g, 90%); LC-MS [M+H]$^+$ 315 (cald. 315.5).

Example XIII 4-n-Butyl-1-[4-(2-methoxymethylphenyl)-4-oxo-1-butyl]piperidine (22)

A 10 mL oven-dried flask was charged with Mg turnings (88 mg, 3.6 mmol) andweactivated under vacuum by the use of a heat-gun. Under inert atmosphere was added a suspension of 1-Iodo-2-methoxymethylbenzene (0.67 g, 2.7 mmol) in Et$_2$O (4 mL) and the reaction mixture was allowed to reflux for 1 hours. A suspension of compound 8 (0.38 g, 1.8 mmol) in CH$_2$Cl$_2$ (4 mL) was added via a syringe and the reaction mixture was stirred at rt overnight. The reaction mixture was quenched by addition of H$_2$SO$_4$ (10 mL, 2 M) and stirred at rt for 2 hours followed by addition of NaOH (10 mL, 2 M). Addition of THF (15 mL) was followed by extraction with ethyl acetate (3×50 mL) and the combined organic phases are washed with brine (10 mL) and NaOH (10 mL, 2 M), and the organic phases were dried (MgSO$_4$) and evaporated to dryness to produce 0.51 g of crude 22. The crude product was subjected to CC [eluent:CH$_2$Cl$_2$:MeOH (99:1)] to give pure 22 (0.14 g, 23%); LC-MS [M+H]$^+$ 331 (cald. 331.5).

Example XIV 4-n-Butyl-1-[4-(2-pyridinyl)-4-oxo-1-butyl]piperidine (24)

4-(4-Butyl-piperidin-1-yl)butyric acid methyl ester (23). To a 25 mL reaction flask was added 4-bromo-butyric acid methyl ester (2.04 g, 11.2 mmol), compound 3 (1.51 g, 10.8 mmol) and potassium carbonate (1.63 g, 11.8 mmol) suspended in CH$_3$CN (10 mL). The reaction mixture was stirred over-night at rt followed by filtration and evaporation to dryness. Addition of H$_2$O (50 mL) was followed by extraction with ethyl acetate (3×100 mL). The combined organic phases were dried (MgSO$_4$) and evaporated to dryness, to produce 2.84 g of crude 23. The crude product was subjected to CC [eluent:CH$_2$Cl$_2$:MeOH (99:1)] to give pure 23 (1.93 g, 75%). LC-MS [M+H]$^+$ 241 (cald. 241.2).

4-n-Butyl-1-[4-(2-pyridinyl)-4-oxo-1-buty lpiperidine (24). To a dry 25 mL reaction flask was added 2-bromopyridine (200 mg, 1.3 mmol) dissolved in CH$_2$Cl$_2$ (3 mL) and the temperature was adjusted to −78° C. After being stirred for 20 min, addition of n-BuLi (0.84 mL, 1.4 mmol) was conducted under inert atmosphere. After additional 30 min, a solution of 23 dissolved in CH$_2$Cl$_2$ (2 mL) was added. The reaction mixture was left to warm to rt over-night before being quenched with H$_2$SO$_4$ (5 mL, 1 M). The reaction mixture was extracted with ethyl acetate (6×25 mL) and the combined organic phases were dried (MgSO$_4$) and evaporated to dryness, to produce 0.31 g of crude 24. The crude product was subjected to CC [eluent: CH$_2$Cl$_2$:MeOH (10:1)] to give pure 24 (75 mg, 12%). LC-MS [M+H]$^+$ 288 (cald. 288.2).

Example XV 4-n-Butyl-1-[4-(2-Hydroxyphenyl)-4-oxo-1-butyl]piperidine (27)

1-Benzyloxy-2-iodo-benzene (25). In a 25 mL ovendried flask 2-iodophenol (1.03 g, 4.7 mmol) and potassium carbonate (0.71 g, 5.2 mmol) were dissolved in dry acetone (10 mL). The mixture was stirred for 15 min followed by addition of benzylbromide (0.61 mL, 5.2 mmol) and left over-night at rt. Addition of H$_2$O (50 mL) followed by extraction with ethyl acetate (3×50 mL) and the combined organic phases were dried (MgSO$_4$) and evaporated to dryness, to produce 1.7 g of crude 25. The crude product was subjected to CC [eluent: Heptane:EtOAc (9:1)] to give pure 25 (1.2 g, 81%). LC-MS [M+H]$^+$ 310 (cald. 310.0).

4-n-Butyl-1-[4-(2-benzyloxyphenyl)-4-oxo-1-butyl] piperidine (26). In a 25 mL oven-dried flask was added Mg turnings (123 mg, 5.1 mmol) which was activated by the use of a heat-gun under vacuum. Under inert atmosphere was added a solution of 1-benzyloxy-2-iodo-benzene (25) (1.18 g, 3.8 mmol) in Et$_2$O (10 mL) and the reaction mixture was allowed to reflux for 3.5 hours. A solution of 4-(4-n-butylpiperidin-1-yl)butanenitrile 4 (0.53 g, 2.5 mmol) dissolved in CH$_2$Cl$_2$ (3 mL) was added and the reaction mixture and was stirred at 40° C. over-night. The reaction mixture was quenched by addition of H$_2$SO$_4$ (10 mL, 2 M) and left stirring for 1 hour, followed by addition of NaOH (20 mL, 2 M) until basic conditions. The reaction mixture was extrated with ethyl acetate (3×50 mL)) and the combined organic phases are washed with brine (10 mL) and NaOH (10 mL, 2 M), and the combined organic phases were dried (MgSO$_4$) and evaporated to dryness to produce 1.28 g of crude 26. The crude product was subjected to CC [eluent: Tol:EtOAc (1:1)] to give pure 26 (0.51 g, 51%); LC-MS [M+H]$^+$ 393 (cald. 393.7).

4-n-Butyl-1-]-[4-(2-hydroxyphenyl)-4-oxo-1-butyl] piperidine (27). To a 25 mL reaction flask was added a solution of 4-n-Butyl-1-[4-(2-benzyloxyphenyl)-4-oxo-1-butyl]piperidine (26) (49 mg, 1.2 mmol) dissolved in dry EtOH (10 mL) and conc. HCl (0.1 mL) followed by addition of palladium on charcoal (40 mg). The reaction flask was then charged with H$_2$ by the use of balloon technique and left stirring at rt over-night under H$_2$ atmosphere. The reaction mixture was basified by addition of NaOH (2 mL, 2.0 M) and filtered through celite. The aqueous phase was extracted with ethyl acetate (3×50 mL) and the combined organic phases were washed with brine (10 mL) and NaOH (10 mL, 2 M), dried (MgSO$_4$) and evaporated to dryness to produce 0.42 g of crude 27. The crude product was subjected to CC [eluent: CH$_2$Cl$_2$:MeOH (99:1)] to give pure 27 (0.21 g, 58%); LC-MS [M+H]$^+$ 303 (cald. 303.2).

Example XVI

Screening of Test Compounds in an Assay Using Muscarinic Receptor Subtypes m1, m2, m3, m4 and m5

Transfection of Cells with Muscarinic Receptor DNAs (General Procedure)

NIH 3T3 cells (available from the American Type Culture Collection as ATCC CRL 1658) were grown at 37° C. in a humidified atmosphere (5% $CO_2$) incubator in Dulbecco's modified Eagle's medium (DMEM) supplemented with 4.5 g/l glucose, 4 mM glutamine, 50 units/ml penicillin, 50 units/ml streptomycin (available from Advanced Biotechnologies, Inc., Gaithersburg, Md.) and 10% calf serum (available from Sigma, St. Louis, Mich.). The cells were treated with trypsin-EDTA, spun down and plated at $2 \times 10^6$ per 15 cm dish in 20 ml of DMEM containing 10% calf serum.

The m1–m5 muscarinic receptor subtypes were cloned substantially as described by Bonner et al., *Science* 237, 1987, p. 527, and Bonner et al., *Neuron* 1, 1988, p. 403. For the m2 and m4 receptors, the cells were co-transfected with DNA encoding a chimera between the Gq protein and the five carboxy-terminal amino acids of the Gi protein (the Gq-i5 construct is described by Conklin et al., *Nature* 363, 1993, p.274).

On day one, the cells were transfected using the Superfect transfection reagent (available from Qiagen, Valencia, Calif.) in accordance with the manufacturer's instructions. Receptor DNA, β-gal DNA (pSI-β-galactosidase available from Promega, Madison , Wis.), chimeric Gq-i5 DNA for the m2 and m4 receptor subtype assays, and salmon sperm DNA (available from Sigma, St. Louis, Mich.) as filler to a total of 20 µg DNA was added per plate. Prior to addition to the plates, 60 µl Superfect was added to the DNA and mixed thoroughly by pipetting up and down several times. The mixture was incubated at room temperature for 10–15 minutes. The media were aspirated, and 12 ml fresh DMEM containing 10% calf serum and 50 units/ml penicillin/streptomycin was added to the plates. The DNA-Superfect solution was mixed once more with a pipette and added to the plate which was swirled to distribute the DNA mixture evenly over the surface. The cells were incubated overnight at 37° C. and 5% $CO_2$.

After incubation, the media were aspirated and the plates were rinsed once with a 15 ml volume of Hank's Buffered Saline. The plates were swirled to ensure thorough rinsing. 20 ml fresh DMEM supplemented with 10% calf serum and 50 units/ml penicillin/streptomycin was added to the plates. The cells were incubated for 24–48 hours until the plates were 100% confluent.

Assay of NIH 3T3 Cells Transfected with Muscarinic Receptor Subtypes (General Procedure)

DMEM containing 2% Cyto-SF3 was heated at 37° C. in a water bath under sterile conditions. Sterile working stock solutions of test compounds to be assayed were prepared by diluting the compounds in DMEM to 8× the final concentration for testing. The compound (carbachol) to be included in the assay as a positive control was also diluted in DMEM to 8× the final concentration. 50 µl of the DMEM containing 2% Cyto-SF3 was added to each well of 96-well microtiter plates under sterile conditions. Then, 16 µl of compound solutions were added to the top wells of the plates, and dilution of the solutions was performed by taking 16 µl of the compound solutions from the top wells and pipetting them into the next row of wells. This procedure was repeated with each subsequent row of wells, except that 50 µl medium alone was added to the baseline control wells (the wells that contain medium and cells, but not test compounds) and plate control wells (wells containing medium, but not test compounds and cells). The plates were then placed in an incubator at 37° C. to equilibrate temperature and pH.

When the cell cultures had reached 100% confluence, the medium was aspirated and each plate was rinsed with 15 ml Hank's Buffered Saline (HBS). The cells were left in the incubator for about 10–15 minutes until the HBS had turned slightly yellow. The HBS was then aspirated and 1 ml trypsin was added to each plate and swirled so as to completely cover the plates. The edges of the plates were gently rapped several times to loosen the cells. After the cells had been dislodged from the surface, 8 ml DMEM containing 10% calf serum and 50 units/ml penicillin and 50 units/ml streptomycin was added to inhibit the trypsin. The plates were rinsed with this medium, and the cells were pipetted into a tube. The cells were centrifuged at 1000 rpm for 5–10 min. in an IEC Centra CL2 centrifuge (produced by Sorvall). Afterwards, the medium was carefuilly aspirated so as not to dislodge the cells. The cell pellet was suspended in 1600 µl DMEM containing 10% calf serum and 50 units/ml penicillin and 50 units/ml streptomycin, after which 20 ml DMEM supplemented with 2% Cyto-SF3 was added. 50 µl aliquots of this cell suspension was added to the wells of the 96-well microtiter plates prepared above (except for the plate control wells). The plates were then incubated for 4 days at 37° C. and 5% $CO_2$.

After incubation, the medium was removed by inverting the microtiter plates and shaking them gently, after which they were blotted on absorbent paper. 100 µl chromogenic substrate (3.5 mM o-nitrophenyl-β-D-galactopyranoside, 0.5% Nonidet NP-40, in phosphate buffered saline) was added to each well, and the plates were incubated at 30° C. until the optimum absorbance at 405 nm was obtained. The asborbance of the baseline and plate control wells were subtracted from all values.

Results

Using the general procedure described above, NIH 3T3 cells were co-transfected with DNAs encoding the m1, m3 and m5 receptor subtypes. A compound library containing approximately 35,000 small organic compounds (1 per well) was screened against the receptors by the procedures described above. FIG. 1 illustrates data from one 96-well plate from the screen. On this plate, two compounds were active at one or more of the transfected receptors. In the total screen, four related compounds were identified that showed activity. To determine which of the receptors were activated in the screen, the compounds were tested as described above against each of the receptors transfected into separate cell cultures. Compound A only activated the m1 receptor subtype, at which it was a potent partial agonist, inducing a lower maximal response than the reference compound carbachol.

In further experiments, the four compounds were found to selectively activate the m1 receptor with no significant activity at the $m^2$, m3, m4 or m5 muscarinic receptors. The most active compound, compound A, was not an antagonist of carbachol-induced responses of the five muscarinic receptor subtypes.

Figure 2:
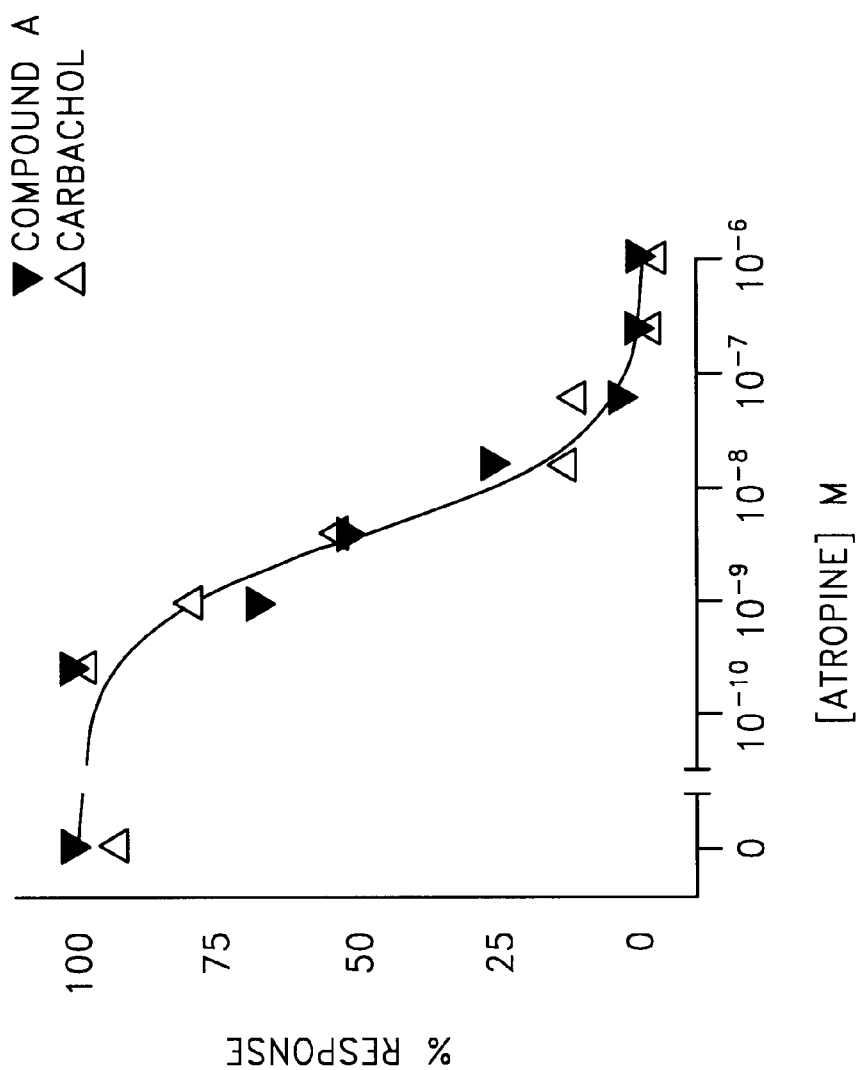
FIG. 2 is a graph showing data comparing the profile of the reference antagonist atropine with m1 muscarinic receptor transfected cells stimulated with either carbachol (open triangles) or compound A (Example I) (closed triangles).

Compound A was further tested for agonist activity against several other receptors at the α-adrenergic receptor subtypes 1D, 1B, 1A, 2A, 2B and 2C, the histamine H1 and the serotonin 5-HT1A and 5-HT2A subtypes. The compound showed no significant activity in these assays. In antagonist experiments, compound A did not inhibit responses of the a-adrenergic receptor subtypes 2A, 2B or 2C, or the serotonin receptor subtypes 5-HT1A or 5-HT2A. As illustrated in FIG. 2, the responses induced by compound A were blocked by the muscarinic antagonist atropine with the same potency as were responses induced by the muscarinic agonist carbachol.

Example XVII

R-SAT Assay

R-SAT assays (see U.S. Pat. No. 5,707,798, incorporated herein by reference) were carried out where cells transfected with m1, m3 or m5 receptors were exposed to seven compounds at 1.5 μM concentration. Cellular response is expressed as a percentage of the maximum response of the cells (defined as response to 10 μM carbachol). The results are presented in the following table.

| Compound | Receptor and Concentration | | |
|---|---|---|---|
| | m1 1.5 μM | m3 1.5 μM | m5 1.5 μM |
| A (Example I) | 107 +/− 9 | 7 +/− 8 | 3 +/− 8 |
| B (Example IX) | 76 +/− 11 | 7 +/− 9 | −6 +/− 10 |
| C (Example XV) | 91 +/− 9 | 4 +/− 9 | 0 +/− 12 |
| D (Example X) | 72 +/− 9 | 13 +/− 7 | 2 +/− 15 |
| E (Example XI) | 42 +/− 13 | 9 +/− 3 | 3 +/− 2 |
| F (Example XII) | 65 +/− 9 | 9 +/− 7 | 5 +/− 11 |
| G* | 66 +/− 19 | 16 +/− 12 | 7 +/− 11 |

*4-n-Butyl-1-[4-phenyl-4-oxo-1-butyl]piperidine

As indicated above, the compounds are selective agonists of the m1 receptor.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

We claim:

1. A compound of formula (I):

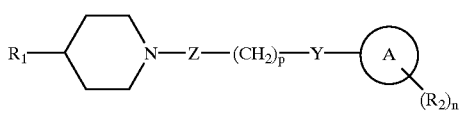

I wherein $R_1$ is straight or branched-chain $C_{2-8}$ alkyl, $C_{2-8}$ alkenyl, $C_{2-8}$ alkynyl, $C_{1-8}$ alkylidene, $C_{1-8}$ alkoxy, $C_{1-8}$ heteroalkyl, $C_{1-8}$ aminoalkyl, $C_{1-8}$ haloalkyl, $C_{1-8}$ alkoxycarbonyl, $C_{1-8}$ hydroxyalkoxy, $C_{1-8}$ hydroxyalkyl, —SH, $C_{1-8}$ thioalkyl, or —O—CH$_2$—$C_{5-6}$ aryl;

A is $C_{5-7}$ cycloalkyl, phenyl, naphthyl or $C_{5-12}$ heteroaryl, wherein said heteroaryl contains one heteroatom selected from O, N or S;

when A is $C_{5-7}$ cycloalkyl, naphthyl or $C_{5-12}$ heteroaryl as defined above, $R_2$ is H, amino, hydroxyl, halo, or straight or branched-chain $C_{1-6}$ alkyl, $C_{2-6}$ alkenyl, $C_{2-6}$ alkynyl, $C_{1-6}$ alkoxy, $C_{1-6}$ heteroalkyl, $C_{1-6}$ aminoalkyl, $C_{1-6}$ haloalkyl, $C_{1-6}$ alkoxycarbonyl, —CN, —CF$_3$, —OR$_3$, —COR$_3$, NO$_2$, —NHR$_3$, —NHC(O)R$_3$, —C(O)NR$_3$R$_4$, —NR$_3$R$_4$, —NR$_3$C(O)NR$_4$R$_5$, —OC(O)R$_3$, or —(CH$_2$)$_q$NR$_3$R$_4$; where $R_3$, $R_4$ and $R_5$ are the same or different, each independently being selected from H, $C_{1-6}$ alkyl; $C_{5-6}$ aryl optionally comprising 1 or more heteroatoms selected from N, O and S, and optionally substituted with halo or $C_{1-6}$ alkyl; $C_{3-6}$ cycloalkyl; or $R_3$ and $R_4$ together with the N atom, when present, form a cyclic ring structure comprising 5–6 atoms selected from C, N, S and O; and q is an integer from 1 to 6; or when A is phenyl, $R_2$ is amino, hydroxyl, chloro, bromo, or straight or branched-chain $C_{1-6}$ alkyl, $C_{2-6}$ alkenyl, $C_{2-6}$ alkynyl, $C_{1-6}$ alkoxy, $C_{1-6}$ heteroalkyl, $C_{1-6}$ aminoalkyl, $C_{1-6}$ haloalkyl, $C_{1-6}$ alkoxycarbonyl, —CN, —CF$_3$, —OR$_3$, —COR$_3$, NO$_2$, —NHR$_3$, —NHC(O)R$_3$, —C(O)NR$_3$R$_4$, —NR$_3$R$_4$, —NR$_3$C(O)NR$_4$R$_5$, —OC(O)R$_3$, or —(CH$_2$)$_q$NR$_3$R$_4$;

where $R_3$, $R_4$ and $R_5$ are the same or different, each independently being selected from H, $C_{1-6}$ alkyl; $C_{5-6}$ aryl optionally comprising 1 or more heteroatoms selected from N, O and S, and optionally substituted with halo or $C_{1-6}$ alkyl; $C_{3-6}$ cycloalkyl; or $R_3$ and $R_4$ together with the N atom, when present, form a cyclic ring structure comprising 5–6 atoms selected from C, N, S and O; and q is an integer from 1 to 6;

n is 1, 2, 3 or 4, the groups $R_2$, when n>1, being the same or different;

p is 0 or an integer from 1 to 5;

Y is —NHC(O)— or —C(O)—; and

Z is a bond or $CR_8R_9$ wherein $R_8$ and $R_9$ are independently selected from H, and straight or branched chain $C_{1-8}$ alkyl;

provided where —(CH$_2$)$_p$—Y— is —(CH$_2$)$_3$—C(O)—, that —A—(R$_2$)$_n$ and $R_1$ are not together: o-methylphenyl and n-butyl, respectively; or a pharmaceutically acceptable salt, ester or prodrug thereof.

2. The compound of claim 1, wherein $R_1$ is straight or branched-chain $C_{2-8}$ alkyl, $C_{2-8}$ alkenyl, $C_{2-8}$ alkynyl, $C_{1-8}$ alkylidene, $C_{1-8}$ alkoxy, $C_{1-8}$ aminoalkyl, $C_{1-8}$ haloalkyl, $C_{1-8}$ alkoxycarbonyl;

n is 1, 2 or 3,

A is phenyl and $R_2$ is chloro, bromo, straight or branched-chain $C_{1-6}$ alkyl, $C_{2-6}$ alkenyl, $C_{2-6}$ alkynyl, $C_{1-6}$ alkoxy, $C_{1-6}$ heteroalkyl; $C_{1-6}$ aminoalkyl, $C_{1-6}$ haloalkyl, $C_{1-6}$ alkoxycarbonyl, —CN, —CF$_3$, —COR$_3$, —NHR$_3$, —NHC(O)R$_3$, —C(O)NR$_3$R$_4$, —NR$_3$R$_4$, —NR$_3$C(O)NR$_4$R$_5$, —OC(O)R$_3$, or —O(CH$_2$)$_q$NR$_3$; or A is thienyl; and $R_2$ is H, halo, straight or branched-chain $C_{1-6}$ alkyl, $C_{2-6}$ alkenyl, $C_{2-6}$ alkynyl, $C_{1-6}$ alkoxy, $C_{1-6}$ heteroalkyl; $C_{1-6}$ aminoalkyl, $C_{1-6}$ haloalkyl, $C_{1-6}$ alkoxycarbonyl, —CN, —CF$_3$, —COR$_3$, —NHR$_3$, —NHC(O)R$_3$, —C(O)NR$_3$R$_4$, —NR$_3$R$_4$, —NR$_3$C(O)NR$_4$R$_5$, —OC(O)R$_3$, or —O(CH$_2$)$_q$NR$_3$; or a pharmaceutically acceptable salt, ester or prodrug thereof.

3. The compound of claim 1 or claim 2, wherein p is 3.

4. The compound of claim 1, wherein said compound of formula (I) is a compound represented by formula (II):

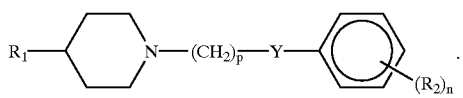

5. The compound of claim 4, wherein said compound of formula (II) is a compound represented by formula (IIa):

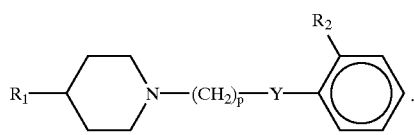

6. The compound of claim 4, wherein said compound of formula (II) is a compound represented by formula (IIb):

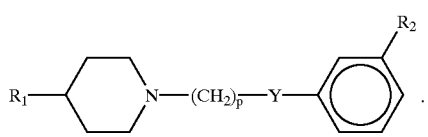

7. The compound of claim 5, wherein $R_1$ is straight or branched-chain $C_{2-8}$ alkyl.

8. The compound of claim 7, wherein wherein $R_2$ is alkyl, aminoalkyl, alkoxy or hydroxyl.

9. The compound of claim 8, wherein wherein p is 3.

10. The compound of claim 9, wherein $R_2$ is methyl, hydroxyl or alkoxy.

11. The compound of claim 10, wherein Y is —C(O)—.

12. The compound of claim 7, wherein $R_2$ is chloro or bromo.

13. The compound of claim 5, wherein $R_1$ is alkoxy.

14. The compound of claim 6, wherein $R_1$ is straight or branched-chain $C_{2-8}$ alkyl.

15. The compound of claim 14, wherein $R_2$ is alkyl, aminoalkyl, alkoxy or hydroxyl.

16. A compound of claim 15, wherein p is 3.

17. The compound of claim 16, wherein $R_2$ is methyl, hydroxyl or alkoxy.

18. The compound of claim 17, wherein Y is —C(O)—.

19. The compound of claim 14, wherein $R_2$ is chloro or bromo.

20. The compound of claim 6, wherein $R_1$ is alkoxy.

21. The compound of claim 1, wherein
Y is —NHC(O)—;
p is 2; and
Z is a bond.

22. The compound of claim 1, wherein
Y is —C(O)—;
p is 3; and
Z is a bond.

23. The compound of claim 21, wherein n is 1 or 2.

24. The compound of claim 2, wherein A is thienyl.

25. The compound of claim 24, wherein Y is —C(O)—.

26. The compound of any one of claims 24 or 25, wherein $R_2$ is halo, $C_{1-6}$ alkyl, or $C_{1-6}$ alkoxy.

27. The compound of claim 24, wherein Y is —NHC(O)—.

28. The compound of claim 5, wherein $R_2$ is halo, $C_{1-6}$ alkyl, or $C_{1-6}$ alkoxy.

29. The compound of claim 25, wherein p is 3.

30. The compound of claim 25, wherein Z is a bond.
31. The compound of claim 29, wherein Z is a bond.
32. The compound of claim 27, wherein p is 2.
33. The compound of claim 27, wherein Z is a bond.
34. The compound of claim 32, wherein Z is a bond.
35. A compound of formula (IIa):

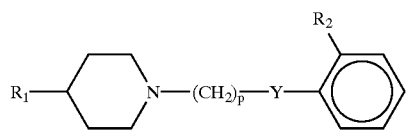

wherein
$R_1$ is alkoxy;
$R_2$ is amino, hydroxyl, chloro, bromo, or straight or branched-chain $C_{1-6}$ alkyl, $C_{2-6}$ alkenyl, $C_{2-6}$ alkynyl, $C_{1-6}$ alkoxy, $C_{1-6}$ heteroalkyl, $C_{1-6}$ aminoalkyl, $C_{1-6}$ haloalkyl, $C_{1-6}$ alkoxycarbonyl, —CN, —CF$_3$, —OR$_3$, —COR$_3$, NO$_2$, —NHR$_3$, —NHC(O)R$_3$, —C(O)NR$_3$R$_4$, —NR$_3$R$_4$, —NR$_3$C(O)NR$_4$R$_5$, —OC(O)R$_3$, or —(CH$_2$)$_q$NR$_3$R$_4$; where $R_3$, $R_4$ and $R_5$ are the same or different, each independently being selected from H, $C_{1-6}$ alkyl; $C_{5-6}$ aryl optionally comprising 1 or more heteroatoms selected from N, O and S, and optionally substituted with halo or $C_{1-6}$ alkyl; $C_{3-6}$ cycloalkyl; or $R_3$ and $R_4$ together with the N atom, when present, form a cyclic ring structure comprising 5–6 atoms selected from C, N, S and O; and q is an integer from 1 to 6;

p is 0 or an integer from 1 to 5;

Y is —NHC(O)— or —C(O)—; or a pharmaceutically acceptable salt, ester or prodrug thereof.

36. A compound of formula (IIb):

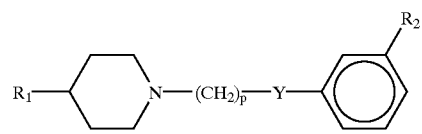

wherein
$R_1$ is alkoxy;
$R_2$ is amino, hydroxyl, chloro, bromo, or straight or branched-chain $C_{1-6}$ alkyl, $C_{2-6}$ alkenyl, $C_{2-6}$ alkynyl, $C_{1-6}$ alkoxy, $C_{1-6}$ heteroalkyl, $C_{1-6}$ aminoalkyl, $C_{1-6}$haloalkyl, $C_{1-6}$ alkoxycarbonyl, —CN, —CF$_3$, —OR$_3$, —COR$_3$, NO$_2$, —NHR$_3$, —NHC(O)R$_3$, —C(O)NR$_3$R$_4$, —NR$_3$R$_4$, —NR$_3$C(O)NR$_4$R$_5$, —OC(O)R$_3$, or —(CH$_2$)$_q$NR$_3$R$_4$; where $R_3$, $R_4$ and $R_5$ are the same or different, each independently being selected from H, $C_{1-6}$ alkyl; $C_{5-6}$aryl optionally comprising 1 or more heteroatoms selected from N, O and S, and optionally substituted with halo or $C_{1-6}$ alkyl; $C_{3-6}$ cycloalkyl; or $R_3$ and $R_4$ together with the N atom, when present, form a cyclic ring structure comprising 5–6 atoms selected from C, N, S and O; and q is an integer from 1 to 6;

p is 0 or an integer from 1 to 5;

Y is —NHC(O)— or —C(O)—; or a pharmaceutically acceptable salt, ester or prodrug thereof.

37. A compound of formula (I):

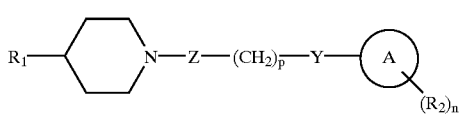

wherein

R$_1$ is straight or branched-chain C$_{2-8}$ alkyl, C$_{2-8}$ alkenyl, C$_{2-8}$ alkynyl, C$_{1-8}$ alkylidene, C$_{1-8}$ alkoxy, C$_{1-8}$ heteroalkyl, C$_{1-8}$ aminoalkyl, C$_{1-8}$ haloalkyl, C$_{1-8}$ alkoxycarbonyl, C$_{1-8}$ hydroxyalkoxy, C$_{1-8}$ hydroxyalkyl, —SH, C$_{1-8}$ thioalkyl, or —O—CH$_2$—C$_{5-6}$ aryl;

A is C$_{5-7}$ cycloalkyl, phenyl, naphthyl or C$_{5-12}$ heteroaryl, wherein said heteroaryl contains one heteroatom selected from O, N or S;

when A is C$_{5-7}$ cycloalkyl, naphthyl or C$_{5-12}$ heteroaryl as defined above, R$_2$ is H, amino, hydroxyl, halo, or straight or branched-chain C$_{1-6}$ alkyl, C$_{2-6}$ alkenyl, C$_{2-6}$ alkynyl, C$_{1-6}$ alkoxy, C$_{1-6}$ heteroalkyl, C$_{1-6}$ aminoalkyl, C$_{1-6}$ haloalkyl, C$_{1-6}$ alkoxycarbonyl, —CN, —CF$_3$, —OR$_3$, —COR$_3$, NO$_2$, —NHR$_3$, —NHC(O)R$_3$, —C(O)NR$_3$R$_4$, —NR$_3$R$_4$, —NR$_3$C(O)NR$_4$R$_5$, —OC(O)R$_3$, or —(CH$_2$)$_q$NR$_3$R$_4$; where R$_3$, R$_4$ and R$_5$ are the same or different, each independently being selected from H, C$_{1-6}$ alkyl;

C$_{5-6}$ aryl optionally comprising 1 or more heteroatoms selected from N, O and S, and optionally substituted with halo or C$_{1-6}$ alkyl; C$_{3-6}$ cycloalkyl; or R$_3$ and R$_4$ together with the N atom, when present, form a cyclic ring structure comprising 5–6 atoms selected from C, N, S and O; and q is an integer from 1 to 6; or when A is phenyl, R$_2$ is amino, hydroxyl, chloro, bromo, or straight or branched-chain C$_{1-6}$ alkyl, C$_{2-6}$ alkenyl, C$_{2-6}$ alkynyl, C$_{1-6}$ alkoxy, C$_{1-6}$ heteroalkyl, C$_{1-6}$ aminoalkyl, C$_{1-6}$ haloalkyl, C$_{1-6}$ alkoxycarbonyl, —CN, —CF$_3$, —OR$_3$, —COR$_3$, NO$_2$, —NHR$_3$, —NHC(O)R$_3$, —C(O)NR$_3$R$_4$, —NR$_3$R$_4$, —NR$_3$C(O)NR$_4$R$_5$, —OC(O)R$_3$, or —(CH$_2$)$_q$NR$_3$R$_4$;

where R$_3$, R$_4$ and R$_5$ are the same or different, each independently being selected from H, C$_{1-6}$ alkyl; C$_{5-6}$ aryl optionally comprising 1 or more heteroatoms selected from N, O and S, and optionally substituted with halo or C$_{1-6}$ alkyl; C$_{3-6}$ cycloalkyl; or R$_3$ and R$_4$ together with the N atom, when present, form a cyclic ring structure comprising 5–6 atoms selected from C, N, S and O; and q is an integer from 1 to 6;

n is 1, 2, 3 or 4, the groups R$_2$, when n>1, being the same or different;

p is 2;

Y is —NHC(O)—; and

Z is a bond; or a pharmaceutically acceptable salt, ester or prodrug thereof.

38. A compound of claim 37 wherein n is 1 or 2.

39. A compound of formula (I):

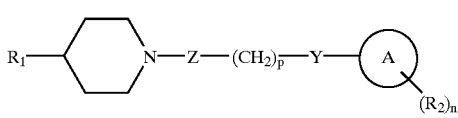

wherein

R$_1$ is straight or branched-chain C$_{2-8}$ alkyl, C$_{2-8}$ alkenyl, C$_{2-8}$ alkynyl, C$_{1-8}$ alkylidene, C$_{1-8}$ alkoxy, C$_{1-8}$ aminoalkyl, C$_{1-8}$ haloalkyl, C$_{1-8}$ alkoxycarbonyl;

n is 1, 2 or 3, the groups R$_2$, when n>1, being the same or different;

A is thienyl; and

R$_2$ is H, halo, straight or branched-chain C$_{1-6}$ alkyl, C$_{2-6}$ alkenyl, C$_{2-6}$ alkynyl, C$_{1-6}$ alkoxy, C$_{1-6}$ heteroalkyl; C$_{1-6}$ aminoalkyl, C$_{1-6}$ haloalkyl, C$_{1-6}$ alkoxycarbonyl, —CN, —CF$_3$, —COR$_3$, —NHR$_3$, —NHC(O)R$_3$, —C(O)NR$_3$R$_4$, —NR$_3$R$_4$, —NR$_3$C(O)NR$_5$, —OC(O)R$_3$, or —O(CH$_2$)$_q$NR$_3$; where R$_3$, R$_4$ and R$_5$ are the same or different, each independently being selected from H, C$_{1-6}$ alkyl; C$_{5-6}$ aryl optionally comprising 1 or more heteroatoms selected from N, O and S, and optionally substituted with halo or C$_{1-6}$ alkyl; C$_{3-6}$ cycloalkyl; or R$_3$ and R$_4$ together with the N atom, when present, form a cyclic ring structure comprising 5–6 atoms selected from C, N, S and O; and q is an integer from 1 to 6; or R$_4$ together with the N atom, when present, form a cyclic ring structure comprising 5–6 atoms selected from C, N, S and O; and q is an integer from 1 to 6;

p is 0 or an integer from 1 to 5;

Y is —NHC(O)— or —C(O)—; and

Z is a bond or CR$_8$R$_9$ wherein R$_8$ and R$_9$ are independently selected from H, and straight or branched chain C$_{1-8}$ alkyl; or a pharmaceutically acceptable salt, ester or prodrug thereof.

40. A compound of claim 39 wherein Y is —C(O)—.

41. A compound of any one of claims 39 or 40 wherein R$_2$ is halo, C$_{1-6}$ alkyl or C$_{1-6}$ alkoxy.

42. A compound of claim 39 wherein Y is —NHC(O)—.

43. A compound of claim 40 wherein p is 3.

44. A compound of claim 40 wherein Z is a bond.

45. A compound of claim 43 wherein Z is a bond.

46. A compound of claim 42 wherein p is 2.

47. A compound of claim 42 wherein Z is a bond.

48. A compound of claim 46 wherein Z is a bond.

49. A pharmaceutical composition comprising an effective amount of a compound of formula (I):

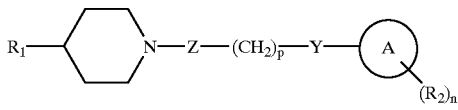

wherein

R$_1$ is straight or branched-chain C$_{2-8}$alkyl, C$_{2-8}$ alkenyl, C$_{2-8}$ alkynyl, C$_{1-8}$ alkylidene, C$_{1-8}$ alkoxy, C$_{1-8}$ heteroalkyl, C$_{1-8}$ aminoalkyl, C$_{1-8}$ haloalkyl, C$_{1-8}$ alkoxycarbonyl, C$_{1-8}$ hydroxyalkoxy, C$_{1-8}$ hydroxyalkyl, —SH, C$_{1-8}$ thioalkyl, —O—CH$_2$—C$_{5-6}$ aryl, —C(O)—C$_{5-6}$ aryl substituted with C$_{1-3}$ alkyl or halo; $C_{5-6}$ aryl or $C_{5-6}$ cycloalkyl optionally comprising 1 or more heteroatoms selected from N, S and O;

A is $C_{5-7}$ cycloalkyl, phenyl, naphthyl or $C_{5-12}$ heteroaryl, wherein said heteroaryl contains one heteroatom selected from O, N or S;

when A is $C_{5-7}$ cycloalkyl, naphthyl or $C_{5-12}$ heteroaryl as defined above, $R_2$ is H, amino, hydroxyl, halo, or straight or branched-chain $C_{1-6}$ alkyl, $C_{2-6}$ alkenyl, $C_{2-6}$ alkynyl, $C_{1-6}$ alkoxy, $C_{1-6}$ heteroalkyl, $C_{1-6}$ aminoalkyl, $C_{1-6}$haloalkyl, $C_{1-6}$ alkoxycarbonyl, —CN, —$CF_3$, —$OR_3$, —$COR_3$, $NO_2$, —$NHR_3$, —$NHC(O)R_3$, —$C(O)NR_3R_4$, —$NR_3R_4$, —$NR_3C(O)NR_4R_5$, —$OC(O)R_3$, or —$(CH_2)_qNR_3R_4$; where $R_3$, $R_4$ and $R_5$ are the same or different, each independently being selected from H, $C_{1-6}$ alkyl; $C_{5-6}$ aryl optionally comprising I or more heteroatoms selected from N, O and S, and optionally substituted with halo or $C_{1-6}$ alkyl; $C_{3-6}$ cycloalkyl; or $R_3$ and $R_4$ together with the N atom, when present, form a cyclic ring structure comprising 5–6 atoms selected from C, N, S and O; and q is an integer from 1 to 6; or when A is phenyl, $R_2$ is amino, hydroxyl, chloro, bromo, or straight or branched-chain $C_{1-6}$ alkyl, $C_{2-6}$ alkenyl, $C_{2-6}$ alkynyl, $C_{1-6}$ alkoxy, $C_{1-6}$ heteroalkyl, $C_{1-6}$ aminoalkyl, $C_{1-6}$ haloalkyl, $C_{1-6}$ alkoxycarbonyl, —CN, —$CF_3$, —$OR_3$, —$COR_3$, $NO_2$, —$NHR_3$, —$NHC(O)R_3$, —$C(O)NR_3R_4$, —$NR_3R_4$, —$NR_3C(O)NR_4R_5$, —$OC(O)R_3$, or —$(CH_2)_qNR_3R_4$; where $R_3$, $R_4$ and $R_5$ are the same or different, each independently being selected from H, $C_{1-6}$ alkyl; $C_{5-6}$ aryl optionally comprising 1 or more heteroatoms selected from N, O and S, and optionally substituted with halo or $C_{1-6}$ alkyl; $C_{3-6}$ cycloalkyl; or $R_3$ and $R_4$ together with the N atom, when present, form a cyclic ring structure comprising 5–6 atoms selected from C, N, S and O; and q is an integer from 1 to 6;

n is 1, 2, 3 or 4, the groups $R_2$, when n>1, being the same or different;

p is 0 or an integer from 1 to 5;

Y is —NHC(O)— or —C(O)—; and

Z is a bond or $CR_8R_9$ wherein $R_8$ and $R_9$ are independently selected from H, and straight or branched chain $C_{1-8}$ alkyl;

provided where —$(CH_2)_p$—Y— is —$(CH_2)_3$—C(O)—, that —A—$(R_2)_n$ and $R_1$ are not together:

o-methyl-phenyl and n-butyl, respectively; or a pharmaceutically acceptable salt, ester or prodrug thereof; and a pharmaceutically acceptable carrier.

50. The composition of claim 49, wherein said compound of formula (I) is a compound represented by formula (II):

51. The composition of claim 50, wherein $R_1$ is straight or branched-chain $C_{2-8}$ alkyl.

52. The composition of claim 51, wherein $R_2$ is alkyl, aminoalkyl, alkoxy or hydroxyl.

53. The composition of claim 52, wherein p is 3.

54. The composition of claim 52, wherein $R_2$ is methyl, hydroxyl or alkoxy.

55. The composition of claim 54, wherein Y is —C(O)—.

56. The composition of claim 51, wherein $R_2$ is chloro or bromo.

57. The composition of claim 50, wherein $R_1$ is alkoxy.

58. The composition of claim 57, wherein $R_2$ is chloro or bromo.

59. The pharmaceutical composition comprising a compound of claim 21.

60. A pharmaceutical composition comprising an effective amount of a compound of formula II:

wherein $R_1$ is alkoxy;

$R_2$ is amino, hydroxyl, chloro, bromo, or straight or branched-chain $C_{1-6}$ alkyl, $C_{2-6}$ alkenyl, $C_{2-6}$ alkynyl, $C_{1-6}$alkoxy, $C_{1-6}$ heteroalkyl, $C_{1-6}$ aminoalkyl, $C_{1-6}$ haloalkyl, $C_{1-6}$ alkoxycarbonyl, —CN, —$CF_3$, —$OR_3$, —$COR_3$, $NO_2$, —$NHR_3$, —$NHC(O)R_3$, —$C(O)NR_3R_4$, —$NR_3R_4$, —$NR_3C(O)NR_4R_5$, —$OC(O)R_3$, or —$(CH_2)_qNR_3R_4$; where $R_3$, $R_4$ and $R_5$ are the same or different, each independently being selected from H, $C_{1-6}$ alkyl; $C_{5-6}$ aryl optionally comprising 1 or more heteroatoms selected from N, O and S, and optionally substituted with halo or $C_{1-6}$ alkyl; $C_{3-6}$ cycloalkyl; or $R_3$ and $R_4$ together with the N atom, when present, form a cyclic ring structure comprising 5–6 atoms selected from C, N, S and O; and q is an integer from 1 to 6;

n is 1, 2, 3 or 4, the groups $R_2$, when n>1, being the same or different;

p is 0 or an integer from 1 to 5;

Y is —NHC(O)— or —C(O)—; or.

a pharmaceutically acceptable salt, ester or prodrug thereof; and a pharmaceutically acceptable carrier.

61. A composition of claim 60, wherein $R_2$ is chloro or bromo.

62. A pharmaceutical composition comprising a compound of claim 37.

63. A method of agonizing a muscarinic receptor comprising contacting said receptor with an effective amount of a compound of formula (I):

wherein $R_1$ is straight or branched-chain $C_{2-8}$ alkyl, $C_{2-8}$ alkenyl, $C_{2-8}$ alkynyl, $C_{1-8}$ alkylidene, $C_{1-8}$ alkoxy, $C_{1-8}$ heteroalkyl, $C_{1-8}$ aminoalkyl, $C_{1-8}$ haloalkyl, $C_{1-8}$ alkoxycarbonyl, $C_{1-8}$ hydroxyalkoxy, $C_{1-8}$ hydroxyalkyl, —SH, $C_{1-8}$ thioalkyl, —O—$CH_2$—$C_{5-6}$ aryl, —C(O)—$C_{5-6}$ aryl substituted with $C_{1-3}$ alkyl or halo; $C_{5-6}$ aryl or $C_{5-6}$ cycloalkyl optionally comprising 1 or more heteroatoms selected from N, S and O;

A is $C_{5-7}$ cycloalkyl, phenyl, naphthyl or $C_{5-12}$ heteroaryl, wherein said heteroaryl contains one heteroatom selected from O, N or S;

when A is C$_{5-7}$ cycloalkyl, naphtyl or C$_{5-12}$ heteroaryl as defined above, R$_2$ is H, amino, hydroxyl, halo, or straight or branched-chain C$_{1-6}$ alkyl, C$_{2-6}$ alkenyl, C$_{2-6}$ alkynyl, C$_{1-6}$ alkoxy, C$_{1-6}$ heteroalkyl, C$_{1-6}$ aminoalkyl, C$_{1-6}$ haloalkyl, C$_{1-6}$ alkoxycarbonyl, —CN, —CF$_3$, —OR$_3$, —COR$_3$, NO$_2$, —NHR$_3$, —NHC(O)R$_3$, —C(O)NR$_3$R$_4$, —NR$_3$R$_4$, —NR$_3$C(O)NR$_4$R$_5$, —OC(O)R$_3$, or —(CH$_2$)$_q$NR$_3$R$_4$;

where R$_3$, R$_4$ and R$_5$ are the same or different, each independently being selected from H, C$_{1-6}$ alkyl; C$_{5-6}$ aryl optionally comprising 1 or more heteroatoms selected from N, O and S, and optionally substituted with halo or C$_{1-6}$ alkyl; C$_{3-6}$ cycloalkyl; or R$_3$ and R$_4$ together with the N atom, when present, form a cyclic ring structure comprising 5–6 atoms selected from C, N, S and O; and q is an integer from 1 to 6; or when A is phenyl, R$_2$ is amino, hydroxyl, chloro, bromo, or straight or branched-chain C$_{1-6}$ alkyl, C$_{2-6}$ alkenyl, C$_{2-6}$ alkynyl, C$_{1-6}$ alkoxy, C$_{1-6}$ heteroalkyl, C$_{1-6}$ aminoalkyl, C$_{1-6}$ haloalkyl, C$_{1-6}$ alkoxycarbonyl, —CN, —CF$_3$, —OR$_3$, —COR$_3$, NO$_2$, —NHR$_3$, —NHC(O)R$_3$, —C(O)NR$_3$R$_4$, —NR$_3$R$_4$, —NR$_3$C(O)NR$_4$R$_5$, —OC(O)R$_3$, —C(O)R$_3$R$_4$, —O(CH$_2$)$_q$NR$_3$, —CNR$_3$R$_4$ or —(CH$_2$)$_q$NR$_3$R$_4$; where R$_3$, R$_4$ and R$_5$ are the same or different, each independently being selected from H, C$_{1-6}$ alkyl; C$_{5-6}$ aryl optionally comprising 1 or more heteroatoms selected from N, O and S, and optionally substituted with halo or C$_{1-6}$ alkyl; C$_{3-6}$ cycloalkyl; or R$_3$ and R$_4$ together with the N atom, when present, form a cyclic ring structure comprising 5–6 atoms selected from C, N, S and O; and q is an integer from 1 to 6;

n is 1, 2, 3 or 4, the groups R$_2$, when n>1, being the same or different;

p is 0 or an integer from 1 to 5;

Y is —NHC(O)— or —C(O)—; and

Z is a bond or CR$_8$R$_9$ wherein R$_8$ and R$_9$ are independently selected from H, and straight or branched chain C$_{1-8}$ alkyl;

provided where —(CH$_2$)$_p$—Y— is —(CH$_2$)$_3$—C(O)—, that —A—(R$_2$)$_n$ and R$_1$ are not together:

o-methyl-phenyl and n-butyl, respectively; or a pharmaceutically acceptable salt, ester or prodrug thereof.

64. The method of claim 63, wherein said compound of formula (I) is a compound represented by formula (II):

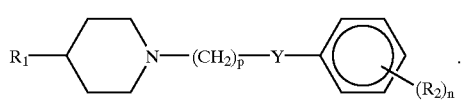

II

65. The method of claim 64, wherein R$_1$ is straight or branched-chain C$_{2-8}$ alkyl.

66. The method of claim 65, wherein R$_2$ is alkyl, aminoalkyl, alkoxy or hydroxyl.

67. The method of claim 66, wherein p is 3.

68. The method of claim 67, wherein R$_2$ is methyl, hydroxyl or alkoxy.

69. The method of claim 68, wherein Y is —C(O)—.

70. The method of claim 65, wherein R$_2$ is chloro or bromo.

71. The method of claim 64, wherein R$_1$ is alkoxy.

72. A method of treating the symptoms of a disease or condition associated with reduced levels of acetylcholine, said method comprising administering a therapeutically effective amount of one or more compounds of claim 1.

73. The method of claim 72, wherein said disease or condition is neurogenerative disease, cognitive impairment, age-related cognitive decline or dementia.

74. A method of treating the symptoms of a disease or condition associated with reduced levels of acetylcholine, said method comprising administering a therapeutically effective amount of a composition of claim 49.

75. The method of claim 74, wherein said disease or condition is neurogenerative disease, cognitive impairment, age-related cognitive decline or dementia.

76. A method of treating the symptoms of a disease or condition associated with increased intraocular pressure, said method comprising administering a therapeutically effective amount of one or more compounds of claim 1.

77. The method of claim 76, wherein said compound comprises a muscarinic receptor agonist.

78. The method of claim 77, wherein said muscarinic receptor agonist comprises m1 receptor agonist activity.

79. The method of claim 77, wherein said muscarinic receptor agonist is m1 selective.

80. The method of claim 79, wherein said agonist causes at least about a 10 fold greater increase in the activity of an m1 receptor subtype than of an m3 receptor subtype.

81. The method of claim 76, wherein said disease is glaucoma.

82. A method of treating the symptoms of a disease or condition associated with increased intraocular pressure, said method comprising administering a therapeutically effective amount of a composition of claim 49.

83. The method of claim 82, wherein said compound comprises a muscarinic receptor agonist.

84. The method of claim 83, wherein said muscarinic receptor agonist comprises m1 receptor agonist activity.

85. The method of claim 83, wherein said muscarinic receptor agonist is m1 selective.

86. The method of claim 85, wherein said agonist causes at least about a 10 fold greater increase in the activity of the m1 receptor subtype than of the m3 receptor subtype.

87. The method of claim 82, wherein said disease is glaucoma.

88. A method of agonizing a muscarinic receptor comprising contacting said receptor with an effective amount of a compound of formula (II):

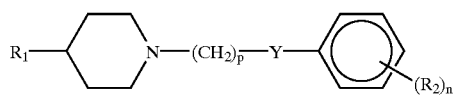

II wherein

R$_1$ is alkoxy;

R$_2$ is amino, hydroxyl, chloro, bromo, or straight or branched-chain C$_{1-6}$ alkyl, C$_{2-6}$ alkenyl, C$_{2-6}$ alkynyl, C$_{1-6}$ alkoxy, C$_{1-6}$ heteroalkyl, C$_{1-6}$ aminoalkyl, C$_{1-6}$ haloalkyl, C$_{1-6}$ alkoxycarbonyl, —CN, —CF$_3$, —OR$_3$, —COR$_3$, NO$_2$, —NHR$_3$, —NHC(O)R$_3$, —C(O)NR$_3$R$_4$, —NR$_3$R$_4$, —NR$_3$C(O)NR$_4$R$_5$, —OC(O)R$_3$, —C(O)R$_3$R$_4$, —O(CH$_2$)$_q$NR$_3$, —CNR$_3$R$_4$ or —(CH$_2$)$_q$NR$_3$R$_4$; where R$_3$, R$_4$ and R$_5$ are the same or different, each independently being selected from H, C$_{1-6}$ alkyl; C$_{5-6}$ aryl optionally comprising 1 or more heteroatoms selected from N, O and S, and optionally substituted with halo or $C_{1-6}$ alkyl; $C_{3-6}$ cycloalkyl; or $R_3$ and $R_4$ together with the N atom, when present, form a cyclic ring structure comprising 5–6 atoms selected from C, N, S and O; and q is an integer from 1 to 6;

n is 1, 2, 3 or 4, the groups $R_2$, when n>1, being the same or different;

p is 0 or an integer from 1 to 5;

Y is —NHC(O)— or —C(O)—; or a pharmaceutically acceptable salt, ester or prodrug thereof.

* * * * *

UNITED STATES PATENT AND TRADEMARK OFFICE
CERTIFICATE OF CORRECTION

PATENT NO. : 6,528,529 B1
DATED : March 4, 2003
INVENTOR(S) : Mark Brann et al.

It is certified that error appears in the above-identified patent and that said Letters Patent is hereby corrected as shown below:

Column 26,
Line 31, "wherein wherein" should be -- wherein --

Column 27,
Line 29, "wherein wherein" should be -- wherein --

Signed and Sealed this

Twentieth Day of April, 2004

JON W. DUDAS
*Acting Director of the United States Patent and Trademark Office*